United States Patent
Sturman et al.

(10) Patent No.: US 11,534,618 B2
(45) Date of Patent: *Dec. 27, 2022

(54) DEFIBRILLATOR COMMUNICATIONS ARCHITECTURE

(71) Applicant: Avive Solutions, Inc., San Francisco, CA (US)

(72) Inventors: Andy Sturman, San Diego, CA (US); David Picco, San Marcos, CA (US); Rory M. Beyer, San Mateo, CA (US); Andrew Thomas Galkowski, San Diego, CA (US); Gordon Moseley P. Andrews, Ross, CA (US); Dean Allan Gereaux, San Diego, CA (US)

(73) Assignee: Avive Solutions, Inc., Brisbane, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/357,498

(22) Filed: Jun. 24, 2021

(65) Prior Publication Data

US 2021/0316152 A1 Oct. 14, 2021

Related U.S. Application Data

(63) Continuation of application No. 16/733,684, filed on Jan. 3, 2020.

(Continued)

(51) Int. Cl.
*A61N 1/39* (2006.01)
*H04W 4/029* (2018.01)
(Continued)

(52) U.S. Cl.
CPC ......... *A61N 1/3993* (2013.01); *A61N 1/3904* (2017.08); *A61N 1/3937* (2013.01);
(Continued)

(58) Field of Classification Search
CPC ....... H04W 4/029; H04W 76/14; H04W 4/80; H04W 4/06; H04W 4/12; A61N 1/3993;
(Continued)

(56) References Cited

U.S. PATENT DOCUMENTS 5,999,851 A 12/1999 White
6,006,132 A 12/1999 Tacker, Jr. et al.
(Continued)

FOREIGN PATENT DOCUMENTS

JP 2016-207159 12/2016
KR 10-1756787 7/2017
(Continued)

OTHER PUBLICATIONS

International Search Report dated Jun. 18, 2020 from International Application No. PCT/US2020/012146.

*Primary Examiner* — Dominic E Rego
(74) *Attorney, Agent, or Firm* — Beyer Law Group LLP

(57) ABSTRACT

Status messages are wirelessly broadcast from medical devices (e.g., defibrillators) as advertisements that don't require the establishment of a wireless connection with listeners. The listeners are configured to act on, or forward, received status messages as appropriate. The listeners may optionally include supplemental information supplied by the listener when forwarding a status message to a management server. The listener may optionally analyze received status messages to determine whether an action should be taken based at least in part on status information in the message. Actions performed by the listener may include initiating a connection with the transmitting device to facilitate uploading new information from the medical device, updating the medical device's firmware, etc. Optionally, some of the advertisements are configured as beacons. The advertisements/beacons may be transmitted using a Bluetooth Low Energy or other suitable protocols. In another aspect, adver- (Continued)

tisement based arrangements for spreading responder network incident alerts are described.

38 Claims, 14 Drawing Sheets

Related U.S. Application Data

(60) Provisional application No. 62/787,872, filed on Jan. 3, 2019.

(51) Int. Cl.
| | |
|---|---|
| *H04W 4/80* | (2018.01) |
| *G16H 40/63* | (2018.01) |
| *H04W 76/14* | (2018.01) |
| *H04L 67/00* | (2022.01) |
| *H04W 4/06* | (2009.01) |
| *H04W 4/12* | (2009.01) |
| *G06F 3/0484* | (2022.01) |

(52) U.S. Cl.
CPC ............ *G16H 40/63* (2018.01); *H04L 67/34* (2013.01); *H04W 4/029* (2018.02); *H04W 4/06* (2013.01); *H04W 4/12* (2013.01); *H04W 4/80* (2018.02); *H04W 76/14* (2018.02); *G06F 3/0484* (2013.01)

(58) Field of Classification Search
CPC .... A61N 1/3904; A61N 1/3937; G16H 40/63; G06F 3/0484
See application file for complete search history.

(56) References Cited

U.S. PATENT DOCUMENTS

| | | | |
|---|---|---|---|
| 7,751,375 | B2 | 7/2010 | Perkins et al. |
| 8,319,632 | B1 | 11/2012 | Vaisnys et al. |
| 8,989,053 | B1 | 3/2015 | Skaaksrud et al. |
| 9,473,941 | B1 | 10/2016 | Palin et al. |
| 10,009,301 | B1 | 6/2018 | Cheng et al. |
| 10,071,256 | B2 | 9/2018 | Montgomery et al. |
| 10,198,967 | B1 | 2/2019 | Agrawal et al. |
| 10,565,845 | B1 | 2/2020 | Beyer et al. |
| 10,737,105 | B2 | 8/2020 | Andrews et al. |
| 10,773,092 | B2 | 9/2020 | Andrews et al. |
| 2003/0055902 | A1 | 3/2003 | Amir et al. |
| 2004/0155772 | A1 | 8/2004 | Medema et al. |
| 2004/0162586 | A1 | 8/2004 | Covey et al. |
| 2005/0036457 | A1 | 2/2005 | Salin |
| 2005/0226201 | A1 | 10/2005 | McMillin |
| 2008/0109302 | A1 | 5/2008 | Salokannel et al. |
| 2008/0136652 | A1 | 6/2008 | Vaisnys et al. |
| 2008/0199894 | A1 | 8/2008 | Galasso |
| 2009/0099866 | A1 | 4/2009 | Newman |
| 2009/0254136 | A1 | 10/2009 | Powers |
| 2011/0006876 | A1 | 1/2011 | Moberg et al. |
| 2011/0082750 | A1 | 4/2011 | Beatty et al. |
| 2011/0087510 | A1 | 4/2011 | Putra et al. |
| 2013/0063758 | A1 | 3/2013 | Saito |
| 2013/0197930 | A1 | 8/2013 | Garibaldi et al. |
| 2013/0030143 | A1 | 11/2013 | Schrader et al. |
| 2013/0295872 | A1 | 11/2013 | Guday et al. |
| 2013/0345768 | A1 | 12/2013 | Vaisnys |
| 2014/0002241 | A1 | 1/2014 | Elghazzawi |
| 2014/0266718 | A1 | 9/2014 | Bongberg et al. |
| 2014/0277224 | A1 | 9/2014 | Quan et al. |
| 2014/0278526 | A1 | 9/2014 | Thakkar et al. |
| 2015/0015401 | A1 | 1/2015 | Wedig et al. |
| 2015/0046491 | A1 | 2/2015 | Clark |
| 2016/0034655 | A1 | 2/2016 | Gray et al. |
| 2016/0066212 | A1 | 3/2016 | Visweswara |
| 2016/0095061 | A1 | 3/2016 | Vainapel et al. |
| 2016/0113595 | A1 | 4/2016 | Bingley et al. |
| 2016/0227392 | A1 | 8/2016 | Palin et al. |
| 2016/0287887 | A1 | 10/2016 | Wu et al. |
| 2016/0354562 | A1 | 12/2016 | Morrison |
| 2017/0056677 | A1 | 3/2017 | Zhang et al. |
| 2017/0071906 | A1 | 3/2017 | Anderson et al. |
| 2017/0091706 | A1 | 3/2017 | Lloyd et al. |
| 2017/0094587 | A1 | 3/2017 | Ding et al. |
| 2017/0156076 | A1 | 6/2017 | Eom et al. |
| 2017/0318622 | A1 | 11/2017 | Yi et al. |
| 2017/0366921 | A1 | 12/2017 | Pflugh et al. |
| 2017/0374533 | A1 | 12/2017 | Batra et al. |
| 2018/0028827 | A1 | 2/2018 | Schilling et al. |
| 2018/0074156 | A1 | 3/2018 | Arunachalam et al. |
| 2018/0091304 | A1 | 3/2018 | Brook et al. |
| 2018/0115574 | A1 | 4/2018 | Ridley |
| 2018/0169426 | A1 | 6/2018 | Montague et al. |
| 2018/0214706 | A1 | 8/2018 | Kutek |
| 2018/0235016 | A1 | 8/2018 | Amschler et al. |
| 2018/0242130 | A1 | 8/2018 | Ganton et al. |
| 2019/0001039 | A1 | 1/2019 | Heide et al. |
| 2019/0075513 | A1 | 3/2019 | Gager et al. |
| 2019/0086508 | A1 | 3/2019 | Isberg et al. |
| 2019/0117983 | A1 | 4/2019 | Andrews et al. |
| 2019/0141485 | A1 | 5/2019 | Ady et al. |
| 2019/0235088 | A1 | 8/2019 | Tanaka et al. |
| 2019/0321646 | A1 | 10/2019 | Wu et al. |
| 2019/0381326 | A1 | 12/2019 | Shahandeh et al. |
| 2020/0098473 | A1 | 3/2020 | Agnello et al. |
| 2020/0215346 | A1 | 7/2020 | Sturman et al. |
| 2020/0221263 | A1 | 7/2020 | Sturman et al. |
| 2020/0253474 | A1 | 8/2020 | Muhsin et al. |

FOREIGN PATENT DOCUMENTS

| | | |
|---|---|---|
| KR | 10-1780214 | 9/2017 |
| WO | WO 2019/126101 | 6/2019 |

US 11,534,618 B2

DEFIBRILLATOR COMMUNICATIONS ARCHITECTURE

CROSS-REFERENCE TO RELATED APPLICATIONS

This application is a Continuation of U.S. patent application Ser. No. 16/733,684, filed on Jan. 3, 2020, which claims the priority of U.S. Provisional Patent Application No. 62/787,872 filed Jan. 3, 2019, all of which are incorporated herein by reference in their entirety.

FIELD

The present disclosure relates generally to methods and arrangements for enabling medical devices such as defibrillators to wirelessly broadcast status and/or other relevant information to other systems, devices and/or modules. Nearby listeners that receive the broadcast messages can act on and/or forward received messages as appropriate.

BACKGROUND

There are a number of use cases where it is desirable for a medical device to be able to transmit information to remotely located servers or systems. For example, automated external defibrillators (AEDs) are typically configured to periodical execute self-tests that check the operational status of the device. It is often desirable to electronically report the results of the self-test and other selected status information to a centralized system and/or the party that is responsible for managing the AED. This is particularly useful for automated external defibrillators because they tend to be stored for prolonged periods of time—often without being checked regularly by their owners. At the same time, it is imperative that the AED be in good working order at the unpredictable times that a cardiac arrest may occur nearby. As such, a number of efforts have been made to directly or indirectly provide AEDs with wired or wireless communication capabilities (such as WiFi or cellular communication capabilities). In some proposals, the communications capability is added directly to the AED itself. In other proposals, the communications capability is provided in a cabinet or docking station that houses or holds the defibrillator. In still others, the communications capabilities are provided by modules that attach to a defibrillator or other devices that can directly monitor or communicate with the defibrillator.

Although existing devices work well, there are continuing efforts to develop AEDs and other medical devices with improved capabilities and features that facilitate the management, use, deployment, availability and/or usability of such devices.

SUMMARY

A variety of methods, devices and communications frameworks are described that facilitate communications from medical devices (e.g., defibrillators) to and with other devices. In one aspect, a defibrillator (or other medical device) communications module is configured to wirelessly broadcast advertisements that each include a status message. The broadcast status messages contain status information about a current status of the defibrillator. The broadcast status messages are suitable for reception and handling by one or more listeners without requiring the establishment of a wireless connection between the communications module and any of the one or more listeners.

The status messages may contain a variety of different status information that is deemed worth of conveying to or through external devices. In various embodiments, status information broadcast by the medical device may include one or more of: (i) a self-test results indicator; (ii) an electrode pads status indicator; (iii) a battery charge level indicator that indicates a charge level of a battery associated with the medical device; (iv) a firmware/software version indicator that identifies the firmware or software version in current use by the medical device; (v) an information available indicator that indicates when the medical device has information that hasn't yet be uploaded; (vi) a device mode indicator that indicates a current operational mode of the medical device (e.g. a standby (stasis) mode, an emergency mode, a training mode, etc.); (vii) a pad type indicator that indicates a type of electrode pad that is currently attached to the defibrillator (e.g., normal (adult), pediatric, training, etc.); (viii) a state identifier that identifies a current state (e.g. an instructional state) of the medical device; (ix) selected incident related information during emergency use of the medical device; and/or (x) other information deemed relevant by the system designers.

In some embodiments, at least some of the advertisements are configured as beacons. Each beacon is configured to cause appropriately configured listeners to perform an action in response to the reception of the beacon without requiring any particular app(s) on the listeners to be open or launched. In some embodiments, the actions may include determining whether it is appropriate to forward a received message to a server and so forwarding the status message when appropriate. In some embodiments, the action is based at least in part on the status information in the status message. In some implementations, the listener may initiate a connection with the defibrillator based on its analysis of the status message, as for example when the status message indicates that the defibrillator has new information available for uploading. In various embodiments, the beacons may take the form of iBeacons, Eddystone beacons, or others.

In some embodiments, the communications module functions as a non-connectable wireless broadcaster when operating in an emergency operating mode and functions as a connectable wireless device when operating in a non-emergency operating mode.

In some embodiments, different information may be transmitted over different advertising channels, or different messages may be alternately transmitted over a single channel. In some embodiments, beacons may be transmitted on a different channel than standard advertisements.

In some embodiments, the communications unit broadcasts status messages more frequently when the medical device is operating in an emergency mode than when the medical device is in a standby mode. In some particular applications, the status messages are broadcast at a frequency of at least once per second when the medical device is operating in the emergency mode.

In some embodiments, the status messages are transmitted over a first channel, and the medical device is configured to establish a wireless connection with a selected listener over a second channel in response to the reception of a connection request from the selected listener.

In some embodiments, the messages that the communications module is configured to broadcast include: (i) a standby status message that is periodically sent when the medical device is in a standby mode; (ii) an emergency status message that is periodically sent when the medical device is in an emergency mode; and (iii) a beacon that is distinct from the standby status message and the emergency status message. In some embodiments, the standby status message and the emergency status message are suitable for handling by one or more associated apps executing on the listener devices and the beacon is configured to cause suitably configured listener devices to perform an action in response to the reception of the beacon without requiring any associated app(s) to be open when the beacon is received.

In another aspect, methods, devices and frameworks are described for handling status messages broadcast by a medical device. The status messages are received wirelessly by the listening device without establishing a connection between the defibrillator and the listening device.

In some embodiments, the listening device is configured to forward at least some of the received status messages to a remotely located management server as appropriate. In some embodiments, the listening device also sends supplemental information supplied by the listening device to the server together with the status message. By way of example, the supplemental information may include (but in not limited to) information such as a timestamp that indicates a time that the status message was received by the listening device and/or location data indicative of the location of at least one of the defibrillator and the listening device.

In some embodiments the receiving server is configured to update a database record associated with the broadcasting defibrillator based on information received from the listener when it is determined that the status message received from the listener was transmitted by the defibrillator more recently than earlier received status messages from the defibrillator based at least in part on the timestamp.

In some embodiments, a GNSS location supplied by the listening device is recorded as a location of the automated external defibrillator.

In some embodiments, the listener is configured to analyze the received status message and determine whether an action should be taken based at least in part on status information in the status message. The action is then performed when it is determined that the action should be taken. In some embodiments, the action(s) taken include requesting or initiating a connection with the medical device. For example, in some embodiments, when the status message includes an information available indicator that indicates that the medical device has new information available, the listener will request or initiate a connection with the medical device. The listener may then retrieve the available information from the medical device. The retrieved information may be forwarded to the management server and/or acted upon by the listener as appropriate.

In another example, in some embodiments, the status message includes a firmware or software version identifiers that indicates a firmware or software version currently operational on the medical device. The listener may optionally be configured to determine whether the firmware or software version currently operational on the medical device is the most recent firmware or software version for the defibrillator. If not, the listener may directly or indirectly causes a firmware or software update available prompt to be generated. Such a prompt may be rendered on the listener or on a separate device associated with an owner or administrator associated with the medical device.

In some embodiments, the firmware or software update is transmitted from the management server to the medical device via the listening device but is not persistently stored on the listening device.

In some embodiments, a Bluetooth Low Energy (BLE) protocol is used to broadcast the advertisements that contain the status messages and/or the beacons that contain status information.

In another aspect, methods, devices and frameworks for spreading responder network incident alerts are described. In some embodiments, a medical device receives an alert indicative of a nearby incident for which the device may be useful. The medical device then broadcasts a wireless incident alert via a beacon or other advertisement suitable for reception and handling by one or more nearby listening devices without requiring establishment of a wireless connection between the broadcasting device and any of the one or more nearby listening device. The broadcast wireless incident alert is configured to cause the one or more nearby listening devices to generate a nearby incident alert. The nearby incident alert informs potential responders (e.g., the listener device's users, bystanders, etc.) that there is a nearby incident for which the medical device (or other alerting device) may be useful. The listener device may have a support app that includes or ties into mapping functionality to show users the location of both the incident and the broadcasting medical device. In some embodiments, the broadcast advertisement is a beacon, as for example, an iBeacon or an Eddystone beacon.

The nearby incident alerts generated by the receiving listening device(s) may include one or more of an auditory incident alert, a visual incident alert and a mechanical incident alert. Some of the described methods are applicable to transmitting devices that are not medical devices.

BRIEF DESCRIPTION OF THE DRAWINGS

The invention and the advantages thereof, may best be understood by reference to the following description taken in conjunction with the accompanying drawings in which.

In the drawings, like reference numerals are sometimes used to designate like structural elements. It should also be appreciated that the depictions in the figures are diagrammatic and not to scale.

DETAILED DESCRIPTION

Figure 1:
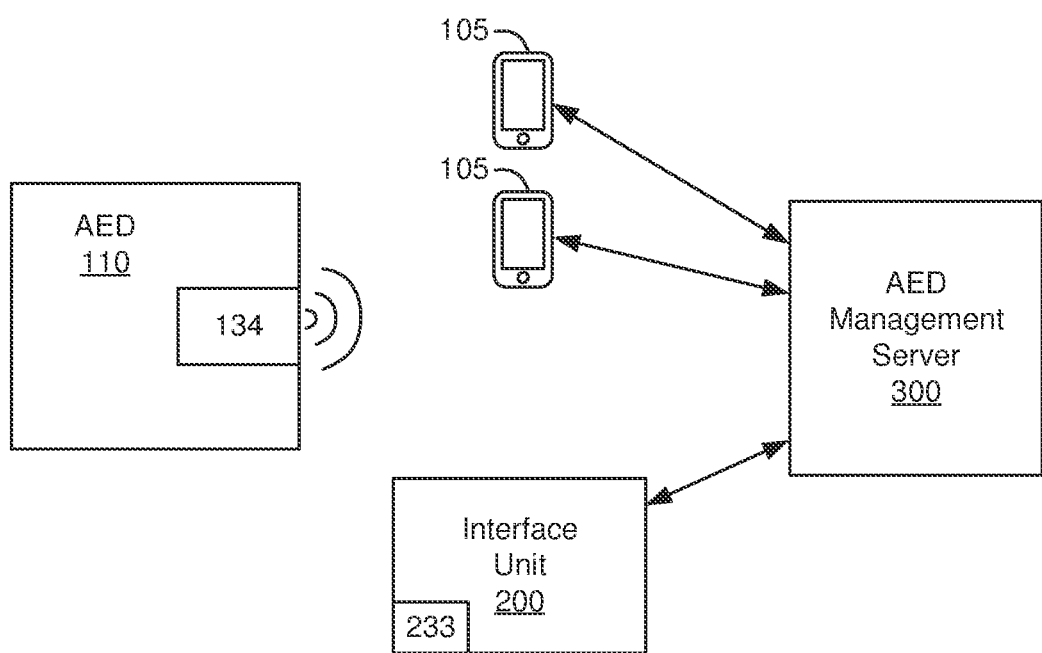
FIG. 1 is a block diagram illustrating components of a system suitable for using low energy broadcasts to convey selected information from an AED to other devices.

The present invention relates generally to methods and arrangements for enabling medical devices such as defibrillators (e.g. automated external defibrillators (AEDs)) to transmit status and other relevant information to other systems, devices and/or modules. More specifically, low energy broadcasts, such as Bluetooth Low Energy (BLE) advertisements are used to convey status messages and/or other messages to nearby listeners that can act on and/or forward received messages as appropriate.

A drawback of many wireless communication protocols and schemes including most cellular and WiFi communication schemes is that they tend to draw a non-trivial amount of power. This can be disadvantageous in the context of medical devices such as AEDs—especially in implementations in which the AED is battery powered and is not expected to be consistently "plugged in" to a power source while it is stored. In particular, frequent use of the cellular, WiFi or similar communications protocols can undesirably drain the battery—which can significantly reduce the defibrillator's unattended shelf-life. Bluetooth and other short range communication protocols tend to have lower energy draws. However, even Bluetooth connections tend to have higher power draws than desirable.

To address the power consumption issue, the present application proposes the use of short range low energy radio frequency (RF) broadcasts to transmit certain types of information (e.g. status messages) from the AED. The low energy broadcasts can be received by any nearby device having an appropriate receiver. Such receiving devices are sometimes referred to herein as "listeners." The listeners can take a wide variety of different forms. For example, the listeners may be: (a) smart phones or other mobile communication devices that happen to be nearby when a broadcast is made; (b) a dedicated device that is affiliated with the AED, such as an interface unit that is attached to the AED itself, a cabinet or dock, or is positioned at any other appropriate location; (c) smart speakers or other IoT devices; or (d) any other suitable device.

The structures of the listeners are not described in detail herein because they can be conventional devices (e.g. smart phones, etc.) having an app, or other suitable software or firmware installed thereon that is suitable for handling the received broadcast messages. In some instances, such services may be provided by a defibrillator support app executing on the listener device, although that is not a requirement.

In general, the listener will include one or more processors configured to execute one or more control algorithms having programmed instructions suitable for causing the listener to perform the desired functions. The listener also includes memory for storing such programmed instructions.

Depending on the context, the receiving device(s) can: 1) forward some or all of the received information to a remotely located server; 2) request the establishment of a connection with the defibrillator (which may be useful to facilitate the transfer of larger blocks of information); 3) act on the information received in another way; and/or 4) handle the received information in any other suitable manner.

In many instances, the listener will evaluate the information received to determine what actions (if any) to take. For example, a status message may include a data available flag that indicates that it has data available that hasn't yet been updated and potentially needs to be transmitted to a server. If the data available flag is set, the listener may request a connection with the AED to allow the AED to transmit the available data to the server via the listener. In another example, a listener can process a received status message to determine whether the status message provides new information that the listener hasn't already forwarded to a defibrillator management server. If the received status message is new, it is then forwarded to the server. Alternatively, if the received status message isn't new (i.e., its contents are the same as a previously received message that has already been forwarded to the server), then the listener may not forward the message to the server again, thereby conserving both power and resources. Of course, there are a variety of other ways that the listener can act on a status message.

Utilizing low energy broadcasts (sometimes referred to as "advertisements") to communicate certain types of status updates, without requiring the establishment of an actual wireless connection between the AED and an external device has several advantages. For example, the low energy broadcasts can be used to communicate the defibrillator's status as the AED waits in a standby mode, thereby reducing the AED's battery usage during the standby mode and increasing the battery's shelf-life. In another example, the broadcasts permit multiple external devices to track the AED's status (as for example during emergency use of the defibrillator) without burdening the AED with establishing and maintaining multiple wireless connections.

Representative components that are suitable for implementing an AED communications framework in accordance with present invention are illustrated in FIG. 1. The core of the system is an AED 110 (also sometimes referred to as a base defibrillation unit) and includes one or more microcontrollers that control the operation of the AED (e.g., defibrillator controller 130). The base defibrillation unit 110 is a fully functional automated external defibrillator. The functionality and/or the communication capabilities of the AED 110 can be supplemented by using the base unit 110 in connection with one or more mobile communication devices 105 (such as Smartphones, tablet computers, etc.) having a defibrillator app installed thereon, or through the use of a dedicated interface unit 200 which is provided in conjunction with the base unit 110. In some embodiments, the interface unit is physically attached to the base unit to form a portable modular defibrillator system (as described, for example, in U.S. patent application Ser. No. 16/145,657 (which is incorporated herein by reference). In other embodiments, the interface unit may be associated with a cabinet or dock that is used to hold/store the AED. In still other embodiments, the interface unit may be a separate detached unit or take any other suitable form.

The base unit 110 includes a wireless communications unit that supports low energy wireless communications. In the illustrated embodiment, the wireless communications unit includes, or takes the form of a Bluetooth module 134 that support Bluetooth Low Energy (BLE) communications. The defibrillator controller 130 (or other suitable controller) communicates with the Bluetooth module 134 and provides the content to be transmitted by the Bluetooth transceiver. Similarly, the mobile communication device 105 and (when present) the interface unit 200 may have Bluetooth communication units 233 that support Bluetooth Low Energy communications. BLE is used in the illustrated embodiment because the vast majority of state of the art cellular phones (and other mobile communication devices) today support Bluetooth and Bluetooth Low Energy. However, it should be appreciated that in other embodiments, additional or alternative wireless communications protocols (especially short-range communications technologies) with appropriate capabilities can be used, including newly developed protocols that may become popular over time.

The mobile devices 105 and the interface unit 200 have long distance communication capabilities that allow them to communicate with remotely located servers such as AED management server 300. Such communications can be made by way of any suitable communications network (e.g., cellular, telephone, satellite, or cable networks, computer networks, the Internet, etc.).

The BLE protocol currently uses 40 radio frequency channels and specifies two channel types—data channels and advertising channels. The advertising channels are used to discover new devices, initiate connections, and broadcast data. The data channels are used to facilitate wireless communication between connected devices. That is, in order to transmit information between devices over a data channel, a wireless connection (session) must be established between the transmitting and receiving devices. In contrast, data broadcast over an advertising channel (sometimes referred to as advertisement data) is broadcast with the expectation that it may (or may not) be received by any listening device and no effort is made to establish a connection (session) between the transmitting and receiving devices to facilitate that data transmission.

In general, advertisements are expected to be relatively short in length. For example, no more than 31 bytes of unrestricted data can be included in an advertisement packet when the BLE 4.1 and 4.2 advertisement protocols are used. A bit more data can be transmitted when the BLE 5.0 or 5.1 advertisement protocols are used and it is likely that future standards may support the transmission of somewhat larger advertising packets. Since the advertisement data is broadcast, the transmitting device generally doesn't know whether the transmitted information was received by any devices, much less any particular target device. Thus, advertisements are not well suited for the transmission of large blocks of information or for the transmission of information whose delivery must be verified.

On the other hand, it typically takes much less energy to transmit relatively small amounts of information in the form of an advertisement than it would to transmit the same information over a formal connection (e.g., as would be required to transmit data over a BLE data channel). This is because of the extra power that is required to establish and maintain a formal wireless connection with a recipient.

In some of the embodiments described below, an AED 110 uses data broadcasts, such as BLE data advertisements, advantageously to facilitate communications with external devices in a variety of emergency and non-emergency scenarios. The specific information transmitted at any time, as well as the relative frequency of the transmitted information may vary widely based on a variety of factors, including the nature of the information to be transmitted, the defibrillator's current operational status, time of day, etc.

The broadcast data can be received by any BLE enabled listener—which facilitates a variety of different use scenario, including several that are not practical or possible with traditional AED communication schemes. Thus, for example, any smart phone (or other mobile device) having suitable BLE listener functionality (e.g. a defibrillator support app or other suitably configured listener app) can receive, and when desired—act appropriately on, the received advertisement(s). This allows devices that are not directly affiliated with or connected to the defibrillator to be used to help facilitate the monitoring, maintenance and/or use of the defibrillator 110. Of course, the broadcast data can also be used by devices that are affiliated with, connected or attached to the AED—such as the defibrillator owner/manager's smart phone or management tablet, a mobile communication device 105 electrically connected to the defibrillator or an interface unit 200—so long as such devices are configured as a BLE listener to receive the AED's broadcasts.

Figure 2:
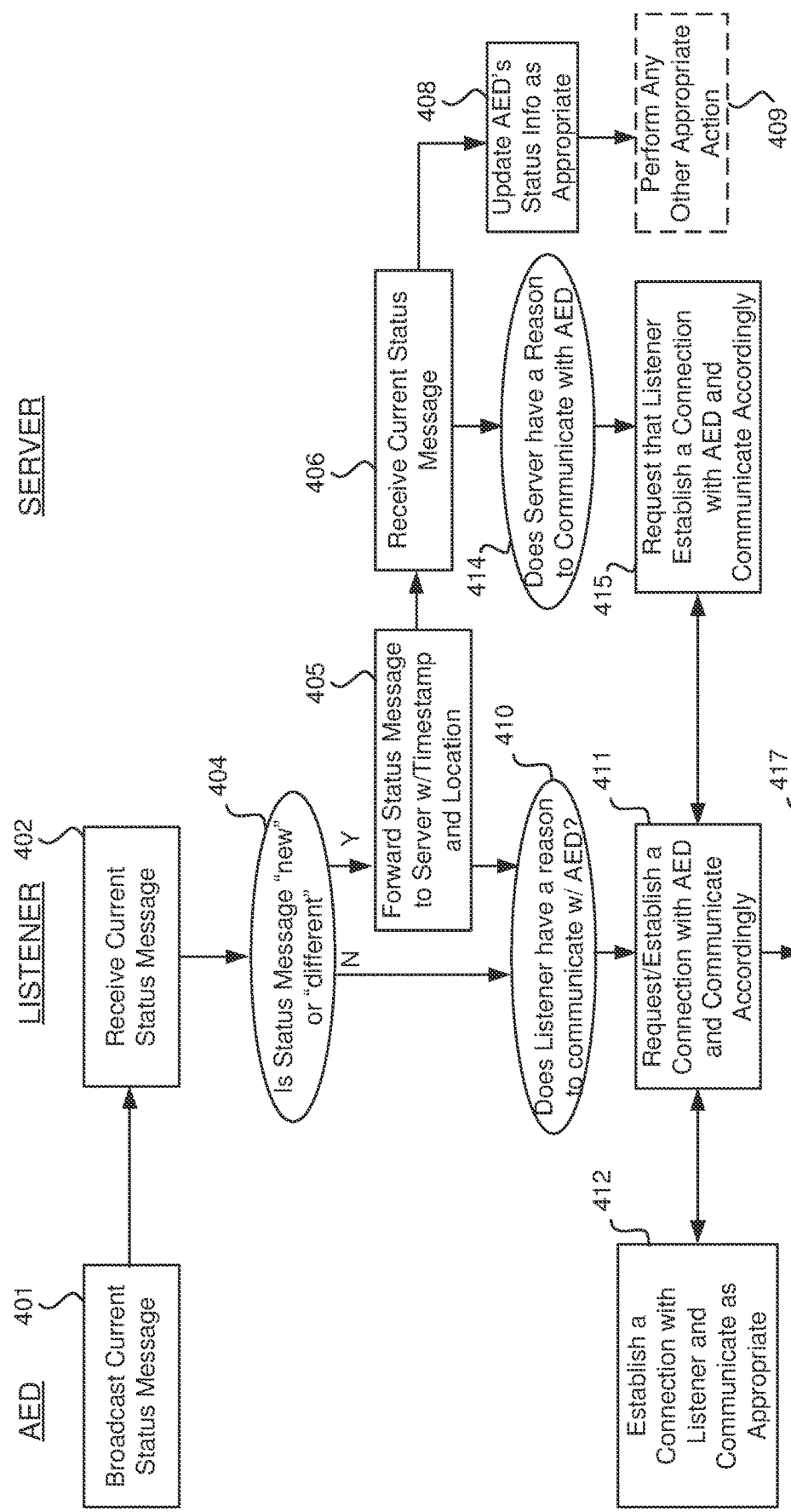
FIG. 2 is a flow chart illustrating a method of communicating status information from an AED to a management server in accordance with one embodiment.

One such use case will be described with reference to FIG. 2. In this embodiment, the AED 110 periodically broadcasts status messages as represented by block 401. The status messages contain selected information about the current status of the AED at the time that the broadcast is made. One type of status message may be sent when the AED is in a stasis or standby mode—i.e., when the AED is sitting available for use but has not been activated to respond to an emergency. The frequency of the standby status message broadcasts can vary widely. In some embodiments, standby AED status messages are broadcast at regular intervals, which could be every second or every few seconds (e.g., every 0.5-5 seconds), every minute or every few minutes, at selected times during the day or at any other desired intervals. In other embodiments, the standby status messages may be broadcast in response to specific triggers such as the AED completing a self-test. In other implementations, a set of spaced apart (in time) status messages may be sent after a triggering event. In practice, there are commercially available BLE transceivers that have extremely low power draws even when broadcasting advertisements at frequencies on the order of every second or two. Therefore, when BLE transceivers are used, the frequency of the advertisement broadcasts does not tend to be a particularly limiting factor on the AED's battery shelf life.

Any listener within range of the AED will receive the status message as represented by block 402. If the listener has a defibrillator support app or other appropriate software that understands the nature of the received status message, the listener will act appropriately on the received message. The appropriate action may vary based upon a variety of factors including any relationship between the listener and the AED (e.g., whether the listener is responsible for the AED, simply a nearby listener that is not associated with the AED, etc.).

In some circumstances, acting appropriately constitutes or includes forwarding the status message on to a designated AED management server 300 as represented by block 405. Preferably, the forwarding is done automatically without requiring any input from a user. In some embodiments, the listener is also configured to automatically provide the server with other relevant information when it forwards the status message to the server. For example, the listener typically adds a unique identifier that identifies itself to the server so that the server knows what intermediary device forwarded the message and can communicate with the forwarding device as may be appropriate. In another example, the listener may add a timestamp that indicates the time that the status message was received. When the listener has GNSS (GPS) capabilities the listener's current location may also be added to the status message when it is forwarded to the server so that the server can determine the approximate location of the AED. The status messages can be forwarded to the server using any suitable communication scheme including synchronous communications, store and forward techniques and/or various other communications protocols.

In some implementations, some level of filtering is done by the listener so that not every redundant instance of a status message is necessarily forwarded to the server. That is, if a number of message instances are received that each have identical content, it is not necessary (and it may be highly undesirable) to forward all such instances to the server since doing so would consume unnecessary resources and power at both the listener and the server. Thus, in some embodiments, the listener will use some predefined logic to determine when to forward a received status message to the server as represented by decision block 404.

In the illustrated embodiment, the listener determines whether the status message is "new" or "different" and therefore worthy of forwarding to the server. (Block 404). The logic used to determine whether to forward a status message to the server may vary based on the nature and needs of any particular implementation. For example, the listener may determine whether the message has any new information relative to the last message that was forwarded. If the received status message contains new information, it is forwarded to the server. (Block 405). In some embodiments, the status message received from the AED may include a timestamp indicating when the last self check was run or provides another unique identifier each time a self check is run, which ensures that the contents of the status message will change each time a self check is run even if the status otherwise remains the same. Regardless of whether a timestamp is used, the listener may only forward the status message when the message contains some different content than the last message that was forwarded to the server (e.g. a new test result) or some other forwarding trigger is activated.

In some embodiments, the listener will also forward a received status message to the server if the listener hasn't forwarded a status message to the server for a designated timeout period. The timeout period can be once a day, once an hour, once every few hours or any other suitable interval.

In still other instances, the listener may receive multiple (potentially many) status reports before it is able to connect with the server. In such circumstances, the listener may be configured to only forward the latest status message when a connection to the server is eventually made. This type of action might be expected if the defibrillator is located outside of cellular data coverage range.

As mentioned above, in some embodiments, the listener may be configured to identify the location of the AED when the status message is forwarded to the server. When the listener provides such location services, it can also forward a status message if/when it determines that the location of AED has changed. This provides a mechanism for informing the server of the AED's movement.

It is noted that it can be difficult for a listener that is not connected to an AED to identify its location based on a single advertising message. However since the AED's BLE advertisements can be expected to have a limited range, a listener that is moving relative to AED can better deduce the location of the AED based on where the reception of advertisements began and ended and/or provide the reception range to the server. The server may use the GNSS locations reported by multiple listeners to more accurately map or verify the AED's location.

When the server receives a status report, it updates its device database if/as appropriate to reflect the current defibrillator status as represented by block 408. The server may also take other appropriate actions (if any) as represented by block 409. The specific actions taken by the server may vary widely based on the nature of the status report and the nature of the services provided by the server. For example, if the AED failed a self-test, needs new electrode pads, needs a battery replacement or charging or other action that requires administrator/owner attention, appropriate messages/notifications can be sent to the owner. Similarly, if the AED has moved from its previous location and has not been returned, it may be desirable to inform the owner/administrator of the movement.

In some instances the status message may include information that triggers either listener or the server to want to establish a connection with the AED to facilitate bidirectional communications with the AED. Alternatively, either the listener or the server may have other reasons to communicate further with the AED. When the listener has reason to communicate further with the AED, it requests/establishes a connection with (e.g. pair with) the AED in response thereto as represented by block 411 and 412. Thereafter, the AED and the listener may communicate with the AED over the established channel as appropriate.

In some circumstances, the server may not have a mechanism for communicating directly with the AED. However, when the server receives a status message from a listener, there is a good chance that the listener is relatively close to the AED and can therefore potentially be used as an intermediary for facilitating communications between the server and the AED. As such, when the server has a reason to communicate with the AED (block 414), it can send a request to the listener to establish a connection with the AED as represented by block 415. When the listener is still within range of the AED, the listener, in turn, may request/establish a connection with the AED 411, 412 as previously discussed. The server can then communicate with the AED via the intermediary listener.

There are a number of use scenarios which may prompt the listener and/or the server to request a connection with the AED. For example, the status message may include a data available indicator 445 (FIG. 3A) that indicates that it has data available for uploading (e.g., for uploading to the server). The listener may optionally be configured to recognize that the data available flag is set and request/establish a connection with the AED in response thereto as represented by block 411. Once the connection is established, the AED may upload its available information and/or take any other appropriate actions as prompted by either the AED itself or by the listener. Often, the uploaded information will be intended for the server and the listener forwards the uploaded information to the server. However, when appropriate, the listener itself can act upon the uploaded information. If the listener doesn't self-initiate a connection with the AED to retrieve the available information, the server will see that there is information available on the AED and will try to establish a connection with the AED through an available channel, such as by requesting that the listener establish a connection (block 415) as discussed above.

Another scenario which may warrant establishing a connection with the AED is when an updated version of the AED's firmware or other software is available. In some implementations, the AED's status message may include firmware/software version indicator 449 that indicates the firmware/software version that the AED is executing. Either the listener or the server may determine that an updated version is available and cause suitable connections to be initiated between the listener and both the AED and server as appropriate to facilitate downloading a software update to the AED. This use case will be described in more detail below. Of course, there are a variety of other situations where either the listener or the server may determine that it is desirable to connect with the AED and communicate therewith as appropriate.

In some specific implementations, all, or virtually all of the electrical components of the AED other than the communications module (e.g. a BLE communications module 134) are turned off when the AED is in a power saving mode. The BLE module includes a clock and an alarm that periodically turns on a power controller. The power controller, in turn, turns on a microcontroller that serves as the defibrillator controller 130 in order to perform a self test. Once the self-test is completed, the defibrillator controller 130 and other electrical components are turned back off and the AED reverts to the power savings mode. As part of the self-test, the defibrillator controller 130 provides the communications module 134 with an updated status message. The updated status message is retained by the communications module 134 and is used as the advertising payload for broadcasts until a new update is received from the defibrillator controller 130—which would typically not occur until the AED is activated again (e.g., to perform the next self-test, for use or for other appropriate reasons). In such circumstances, a listener that is located close to the AED may receive a large number of identical status messages and there is no need to forward the received message to the management server more than once. In other circumstances, a designated waiting period may be required before a listener will forward a newly received status message instance that is identical to the last forwarded status message.

Although the described forwarding is quite simple to implement, this approach has several noteworthy features. One such feature is the ability of nearby or passing devices, including cell phones, to forward the status message without requiring any input by the cell phone's owner. There are a number of use scenarios that this supports. For example, if the AED is stored in a home or office location, the owner or responsible administrator or other interested individual (and thus their cell phone or other mobile communication device) may be nearby at times and therefore receive a broadcast message. The receiving device then automatically forwards the received message to the AED management server 300 thereby updating the AED's status within the server's AED management database. All of this is done without requiring any special effort by the owner/administrator other than initially installing the defibrillator app on their mobile device(s) and allowing the app to run in the background. This enables remote monitoring of the AED's status even when neither the defibrillator nor its cabinet/dock has any wired or wireless long distance communications capabilities. It also provides a mechanism for pinpointing/confirming the location of an AED, which is particularly useful when the AED is otherwise non-connectable.

Even when the AED is stored in a more public locations, the AED can be remotely monitored using the described approach. For example, when the AED is stored in a building lobby or hallway, at a sports field, in a vending machine (as is common in Japan) or in any other public location, it will likely be positioned in an accessible location where it will be seen by passersby. If a passerby having an appropriate listener installed on their mobile device is in the vicinity when a status message is broadcast, the passing mobile device will receive and forward the status message to the AED management server. In this manner, the status message can be virally forwarded to the AED management server without having to involve the AED's owner/administer. Again, this provides a mechanism for allowing remote monitoring of AEDs that don't have their own long distance communication capabilities.

It should be noted that there is no expectation that every status message will necessarily be received by a listener and others may be received by multiple listeners. Indeed, it should be expected that in some installations, the probability that any specific instance of a status message may be received and forwarded by a listener may be quite low. To increase the probability that any particular message will be forwarded, the AED may rebroadcast the message multiple times—as for example, every second, every few seconds or minutes, at different times of day, hourly, etc. The repetition scheme chosen for any particular installation may vary based on a variety of factors.

It should be appreciated that it is not necessary for every transmitted status message to make its way to the server. Although regular updates are desirable, given the nature of AEDs, in many installations it is not necessary that a status update be received by the management server every day, or even every week. Therefore, even if status messages are received by a listener and forwarded to the management server relatively infrequently, the AED can still be monitored much more effectively than AEDs without the communication capabilities as long as some messages get through. Furthermore, if no updates are received for an extended period of time, the AED management server can send a message to the AED's owner/administrator requesting that they check the defibrillator's status.

It should also be appreciated that each broadcast status message broadcast only sends the most recent status information. Therefore, the information received by the listener (and forwarded to the management server) is always the most up-to-date status information available. The management server can also use the timestamp that the listener added to the status message to help verify that the received information is the most recent information. Thus, if there is a delay between a listeners reception of a status message and its ability to forward that message to the server, the server can determine that a just received status message is actually older than an earlier received status message and act accordingly (e.g., not act on the older information).

The listener's geo-location may be used by the AED management server to approximate the location of the AED. The management server can utilize this information to determine if/when the AED has been moved and/or to verify that the AED remains at its designated location. If the AED is a public access AED, the AEDs location can then be identified, verified and/or updated as appropriate on a public access AED map. The location information attained in this manner can also be used by a responder network App to navigate a responder to the AED in the event that there is a nearby cardiac arrest incident.

In situations where a long distance communication module or unit or the like (such as interface unit 200) is provided with the AED or its storage cabinet, the AED may communicate with the communications module using the same broadcast approach. This helps facilitate a truly modular design where the same AED can support remote monitoring regardless of whether or not it has its own associated long distance communication module. When a listener (such as an interface unit or the administrator's mobile device) is associated with the AED, the defibrillator app running on the listener may independently utilize and/or act on the received status information in addition to, or in place of forwarding the status message to the management server 300.

As mentioned above, the specific information transmitted in a status message may vary widely based on a variety of factors including the AED's current operating state, system design preferences, etc. For example, the types of information transmitted when the AED is in a non-emergency standby mode many be very different than the types of information transmitted when the AED is being used in an emergency mode to treat a potential cardiac arrest incident.

Figures 3A, 3B:
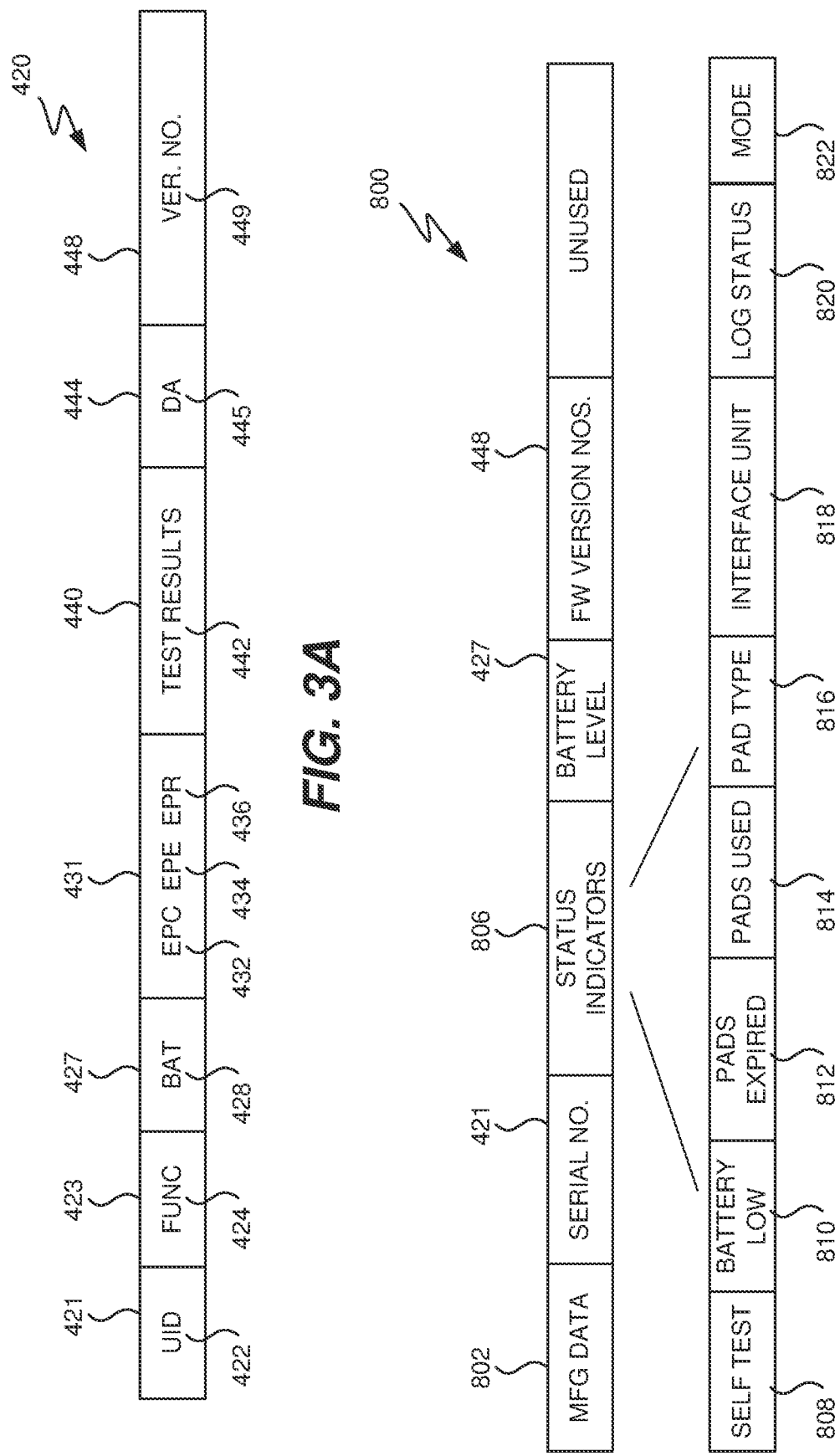
FIG. 3A is a diagrammatic illustration of the contents of a standby status message in accordance with a first embodiment.
FIG. 3B is a diagrammatic illustration of the contents of a standby status message in accordance with another embodiment.

FIG. 3A illustrates the contents of a standby status message in accordance with one specific embodiment. In this embodiment the fields of the status message's data structure 420 include: (1) an AED identifier field 421; (2) a functionality status field 423; (3) a battery level field 427; (4) an electrode pads status field 431 that contains one or more status indicators relating to the status of the electrode pads; (5) a self-test results field 440; (6) a data available field 444; and (7) a firmware/software version field 448.

The AED identifier field 421 includes a unique device identifier 422 such as the AED's serial number or other information that uniquely identifies the defibrillator. If the serial number is particularly long as is common in medical devices, a unique segment of the serial number that uniquely identifies the AED with respect to other AEDs that have broadcasting abilities may be used.

The functionality status field 423 contains a functionality status indicator 424 that indicates whether the AED is currently in a functional state. That is, whether the AED is working properly. In various embodiments, the functionality status indicator may take the form of a flag or other suitable data structure.

The battery level field 427 contains a battery level indicator 428 that indicates the charge level of the AED's internal battery. The charge level may be represented in any suitable form, as for example as a percentage of a full charge remaining.

The electrode pads status field 431 contains one or more status indicators relating to the status of the electrode pads. For example, in the illustrated embodiment, the status indicators include: (a) an electrode pads connected/disconnected indicator 432 that indicates whether electrode pads are currently connected to the AED; (b) an electrode pads expiration indicator 434 that indicates whether the AED's electrode pads have expired and/or when they will expire; (c) an electrode pads replacement indicator 436 that indicates whether the electrode pads need to be replaced; and/or (d) an installed pad type indicator (not shown) that indicates the type of pads installed—e.g., normal (adult), pediatric, training, etc. Any of these electrode pad related indicators may take the form of a flag or other suitable data structures. If the expiration date of the pads is provided, the electrode pad expiration indicator can take the form of the expiration date. Of course, in other embodiments, not all of these electrode pads related indicators are required and/or other different indicators may be provided. In another example, the pads connected/disconnected indicator could further indicate the type of the connected pads (e.g., normal pads, pediatric pads, brand A or brand B pads, etc.)

The self-test results field 440 includes a self-test indicator 442 that indicates whether the AED passed or failed its latest self-test. In some embodiments, the self-test indicator may take the form of a flag. In others, the self-test indicator or another available field may provide additional information regarding the reason for any failure of the self-test.

The data available field 444 includes a data available indicator 445 that indicates that the defibrillator has information available to be uploaded to the AED management server or other appropriate location. The data available indicator may take the form of one or more flags or other suitable data structure. Preferably the flag will be reset if/when the available data is successfully uploaded to the server. In some implementations multiple distinct flags/indicators may be used to indicate the type of information that is available for upload. For example, a first flag can indicate that the defibrillator has been used in a treatment event and has incident related data available for uploading. A second flag can indicate that the AED has self-test data to report. Other flags can be used to indicate other types of information that may be available from the defibrillator.

The firmware/software version field 448 includes a version indicator 449 that indicates the firmware or software version that is currently installed on the AED. The AED management server can utilize the software version to determine whether the software installed on the defibrillator is out of date and needs to be updated. In some implementations the firmware may be divided into multiple discrete components that may be individually loaded. This can be advantageous so that the entire firmware bundle doesn't need to be uploaded for every firmware update. When such an approach is used, the version indicator 449 may optionally be a concatenation of version identifiers for different components.

FIG. 3B illustrates an alternative standby advertising message structure. In this embodiment, the fields of the status message's data structure 800 include: (1) a manufacturer field 802, (2) an AED identifier field 421; (3) a set of status indictors field 806; (4) a battery level field 427; and (5) a firmware version field 448.

The manufacturer field 802 includes a manufacturer ID and any other appropriate manufacturer data. The AED identifier field 421, the battery level field 427 and the firmware version field 448 may be similar to those described above. The status indicators field 806 includes a number of status indicators.

The specific status indicators employed may vary based on the needs of the system, and may include any of the status indicators discussed above with respect to FIG. 3A as well as any other desired indicators. In a particular embodiment, the status indicators include a self test flag 808, a battery low flag 810, a pad expired flag 812, a pads used flag 814, a connected pad type indicator 816, an interface unit flag 818, a log status flag 820, and a device mode indicator 822. Of course any of the flags may be implemented as other types of indicators and vice versa as desired.

The self test flag 808 indicates whether any self test has failed since the flag was last reset. The battery low flag 810 indicates whether or not the battery charge level is low. The pad used flag 814 indicates whether or not the pads have been used. The connected pad type indicator 816 indicates the type of pads that are attached. For example, the connected pad type indicator may indicate whether no pads are attached, normal pads are attached, pediatric pads are attached or training pads are attached. The interface unit flag 818 indicates whether an interface unit (such as described in the incorporated patent application Ser. No. 16/145,657) is attached to or included with the AED. Log status flag 820 may serve as the data available indicator 445 to indicate whether has a self-test log (or potentially other data) available that has yet to be uploaded. The device mode indicator 822 indicates the current operational mode of the defibrillator (e.g., whether the AED is currently in a standby or emergency operating mode).

Although some specific status message data structures have been described, it should be appreciated that not all of the described indicators are required in any particular embodiment and that a variety of other indicators and information can be conveyed in place of or in addition to the described indicators. For example, in some embodiments it may be desirable to indicate information such as the date and time of latest firmware installation; the AED's hardware version number; the results of a set of more than one self-tests (e.g., the last 30 days); etc.

Figure 4:
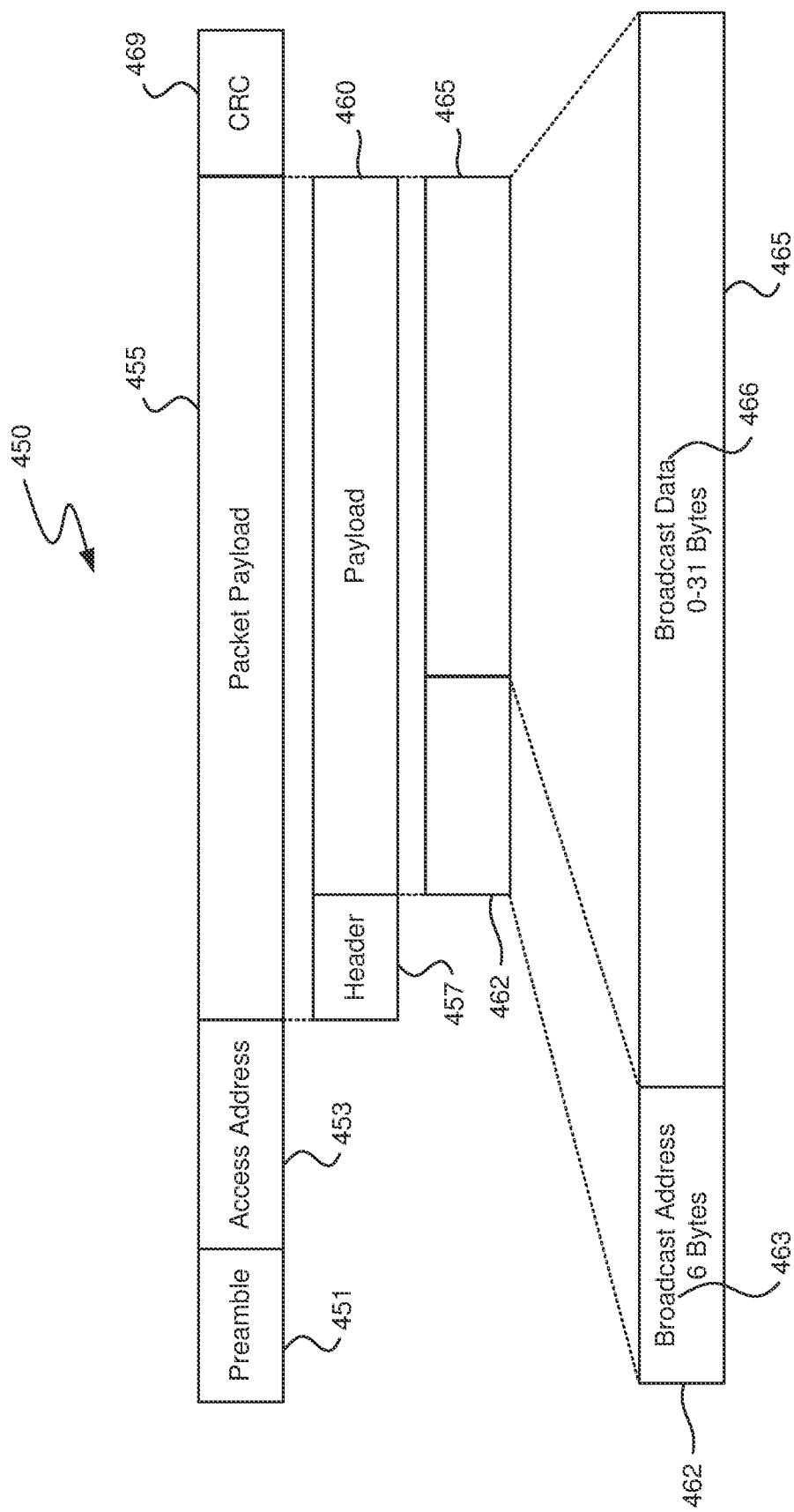
FIG. 4 is a diagrammatic illustration of a representative Bluetooth Low Energy (BLE) packet that may be used to transmit status messages.

FIG. 4 illustrates the structure of a representative BLE packet 450 that includes the status message 420. The illustrated packet structure is compatible with the BLE Specification Version 4.1 standard. The first Byte of the package is a Preamble field 451 which is followed by an Access Address field 453 that is four Bytes long. The Access Address field 453 is followed by a variable length Packet Payload 455, which is followed by a three Byte long Error Detection Code (CRC field 469) which contains a cyclic redundancy check (CRC).

The Packet Payload 455 is small and can vary in length between 2 and 39 Bytes long. The first two Bytes of Packet Payload 455 are a header field 457 with the remaining 0-37 Bytes being referred to as the Payload 460. The header field 457 provides information about the nature of the advertisement being sent—e.g., whether the advertisement is undirected or directed at a particular device. The header field also indicates whether the transmitting device (i.e., AED 110) is available for BLE connections.

The first 6 Bytes of the Payload 460 is the Broadcast Address field 462 which contains the address 463 of the broadcasting device (i.e., the AED 110 in this embodiment). The Broadcast Address 463 can be used by the listening device to establish a connection with the broadcasting AED if and when desired. The remaining 0-31 Bytes of the Payload 460 is the Broadcast Data field 465, which contains the Broadcast Data which is sometimes referred to as Advertising Payload 466.

The Advertising Payload 466 contains the information that the defibrillator 110 seeks to broadcast to nearby listening devices, such as mobile communication device 105, interface unit 200, etc. Thus, for example, when the AED is in a non-emergency standby mode, the Advertising Payload 466 may take the form of AED status message 420 or 800 described above.

The description above is of a packet format compliant with the BLE Specification Version 4.1 standard. As will be familiar to those skilled in the art, other BLE standards such as BLE 5.1 have somewhat different packet structures which may be used in alternative embodiments. A particular advantage of BLE 5.1 is that it permits larger advertising packet payloads.

Figure 5A:
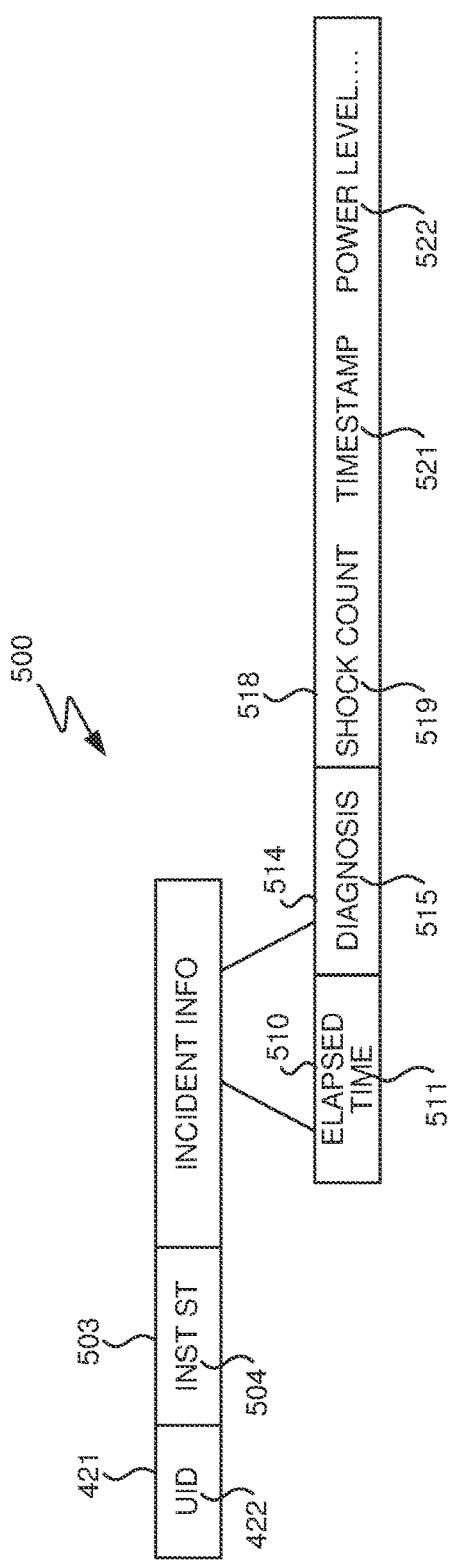
FIG. 5A is a diagrammatic illustration of the contents of a status message suitable for broadcasting during emergency use of an AED in accordance with an embodiment.

When the defibrillator is operating in an emergency mode it may be desirable to broadcast some different types of information in the Advertising Payload 466. Referring next to FIG. 5A, a defibrillator status message 500 suitable for broadcast during emergency use of the defibrillator in accordance with a first embodiment will be described. In the embodiment illustrated in FIG. 5A, the emergency mode status message 500 includes: (1) the AED identifier field 421; (2) a state field 503; and optionally (3) various incident related information. In some embodiments, a message format field (not shown) having an identifier that identifies the type or format of the message is provided. The message format identifier is particularly useful in circumstances in which the message payload can contain different content at different times. When a message format identifier is provided, the listener can determine the type of message that is received based on the value of the message format identifier and can therefore interpret the message appropriately.

The AED identifier field 421 may include a unique device identifier 422 as previously discussed. In other embodiments, the AED identifier field 421 may include an identifier that simply identifies the transmitting device as an AED in general without uniquely identifying the device.

In some implementations each instruction that can be issued by the AED during emergency use of the defibrillator is assigned a unique instruction state identifier. The state field 503 includes a state identifier 504 that corresponds to the current event state of the AED. Some of the available event states are instruction states. Therefore, any listening device that receives the status message 500 knows the AEDs current instruction state. The instructional state may be used to facilitate the display of graphic instructions on the listening device that are synchronized with audio instructions issued by the AED. Such a system is sometimes referred to herein as "in sync graphics" and is described in detail in U.S. patent application Ser. No. 16/145,657 which is incorporated herein by reference. Although instruction states are an important set of the potential defibrillator states, it should be appreciated that the set of available states is not limited to instruction states. Rather, there may be any number of defibrillator states that are not associated with any particular instruction.

When the AED is activated for emergency use, the AED broadcasts the emergency mode status message 500 at regular intervals. The specific intervals used may vary but they are preferably fairly frequent. By way of example, frequencies on the order of several status messages per second works well (e.g. 3-20 Hz). In one specific example, status messages are sent every 0.1 seconds (i.e., at a frequency of 10 Hz).

Each status message includes the current defibrillator state (which may be one of any of a number of instruction states) so any active listeners within range of the AED are informed of the current instruction state of the AED and can act accordingly. If the listener has a display screen and is being used in conjunction with the AED, the defibrillator app uses the current instruction state identifier to identify content to be displayed on the display screen. The displayed content may take any suitable form, as for example, a GIF, an image, textual materials, a short video or any other displayable information, or combinations thereof. These types of content are collectively referred to as graphics herein. When the AED transitions to a new instruction state, the state identifier 504 is updated to reflect the new instruction state in the next transmitted status message 500, thereby informing all listening devices of the update. Any listening device that is rendering in-sync graphics can then transition to the graphic that is appropriate for the new instruction state. A representative in-sync graphics rendering scheme will be described in more detail below with respect to FIG. 9.

A noteworthy feature of the described broadcasting of the emergency mode status messages 500 is that the messages can be received by any listening device that is within range of the AED without requiring the use of defibrillator resources to establish and/or maintain communication sessions (connections) therewith. Therefore multiple devices can independently render the in-sync graphics at the same time. Thus if several people that have a defibrillator app installed on their Smartphones arrive at the scene of a cardiac arrest incident, they can each follow the AED's progress on their own device, thereby potentially facilitating better patient care. This is a notable characteristic that is not possible with conventional commercially available defibrillators.

Furthermore, if the responders speak different languages (e.g., one responder speaks English, another Spanish and a third speaks Chinese), their respective devices can render the graphics in the appropriate languages. This works because the state identifier 504 identifies the instruction state rather than trying to pass the relevant graphics and the defibrillator app looks up the instructions that correspond to that instruction state—preferably from a locally stored table or database. In the English language version of the app, any textual materials in the graphics can be in English—whereas in the Spanish language version of the app, the textual materials in the graphic can be in Spanish. Similarly, if the listener device is in Chinese, it can render the sync graphics in Chinese, even if the AED is providing audio instruction in a different language—such as English. This feature can be particularly beneficial in international cities that have residents and/or visitors that speak a variety of different languages.

Returning to FIG. 5A, the incident related information that is conveyed as part of a status message 500 may vary widely as appropriate for any particular implementation. In general, the incident related information conveyed is a set of information that is believed to be most useful to a responding emergency medical technician (EMT) at first glance. If the EMT or other authorized medical personnel desires more information about the incident, they can connect to the AED (via a wired or wireless connection) to request or obtain additional information. In the embodiment illustrated in FIG. 5A, the incident related information includes an elapsed time field 510, a rhythm diagnosis field 514 and a shock count field 518. In other embodiments, more or fewer information fields may be provided.

The time elapsed field 510 includes an elapsed time identifier 511 that indicates the amount of time that has elapsed since the AED was activated. In other embodiments, the time elapsed field may include a timestamp or equivalent indicating the time that the AED was activated and a current timestamp so that the receiving device itself can determine the elapsed time.

The rhythm diagnosis field 514 includes a rhythm identifier or diagnosis 515 that indicates the type of cardiac rhythm that has been identified by the AED's classifier (e.g., ventricular fibrillation (VF), ventricular tachycardia (VT), etc.). In some implementations multiple rhythm identifications can be provided. For example, it may be desirable to provide an original (pre-shock) rhythm diagnosis in addition to the current rhythm diagnosis. If multiple shocks have been delivered, it may be desirable to provide the original rhythm classification together with the diagnosis that was made after each administered shock including the current rhythm diagnosis (e.g., normal, VF, VT, etc.).

The shocks count field 518 includes a shock count identifier 519 that indicates the number of shocks that have been delivered as part of the current incident. In some embodiments, the shock count identifier 519 may be followed by shock information that identifies the timing and nature of each delivered shock. The specific shock information provided may vary widely based on the design goals and needs of any particular systems. By way of example, in some embodiments, for each administered shock, a timestamp 521 and a power level indicator 522 provided. The timestamp 521 indicates the time that the shock was delivered. The power level indicator 522 indicates the energy level associated with the shock. In some embodiments, other relevant information such as they type of electrode pads used (e.g., normal or pediatric), etc. may be provided as well.

Figure 5B:
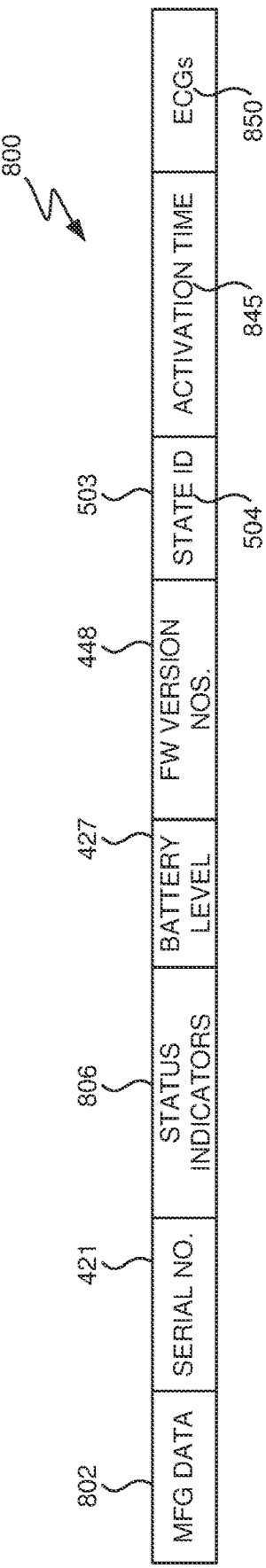
FIG. 5B is a diagrammatic illustration of the contents of a status message suitable for broadcasting during emergency use of an AED in accordance with another embodiment.

Referring next to FIG. 5B, an alternative emergency advertising message structure 840 will be described. In this embodiment, the initial portion of the message structure is identical to the initial portion of the standby message structure. For example, when the standby advertising message has the structure of FIG. 3B, the emergency advertising message structure includes the same fields, plus some additional fields. The repeated fields of include: (1) the manufacturer identifier 802, (2) the AED identifier field 421; (3) the set of status indictors field 806; (4) the battery level field 427; and (5) the firmware version field 448. In the embodiment of FIG. 5B, the additional fields include an event ID field 503, an activation time field 845 and one or more Shock Info fields 850 (sometimes referred to as ECG fields).

The event ID field 503 stores a state identifier 504 which may be similar to the state identifier described above with respect to FIG. 5A. As pointed out above, the identified state may be an instruction state or one of a variety of other defibrillator states. That is, there may be defibrillator states that are not associated with a particular instruction. The activation time field 845 includes a timestamp 846 that indicates the time that the AED was activated in connection with the present incident. The Shock Info fields 850 store identifiers indicative of the selected ECG and shock related parameters. The specific identifiers used may vary widely based on developer design choices. In a particular implementation, each ECG identifier is associated with a particular ECG shock analysis. The identifiers include a shock decision, a child/adult indicator and a timestamp. The shock decision indicates whether the ECG was identified as shockable or not shockable. The child adult indicator indicates whether the AED was in a normal or pediatric mode. The timestamp indicates the time (e.g. minutes or seconds) since the AED was activated until the associated shock was delivered, or when appropriate, a decision was made not to deliver a shock based on the associated ECG analysis. In some embodiments, the ECG identifier may also have an energy level indicator that indicates the nominal (or measured) energy delivered by the associated shock (e.g., 150 joules, 180 joules, etc.).

In some embodiments, the Incident ID field (discussed below) may also be included in the emergency status message. The incident ID field provides a unique Incident ID. The Incident ID can be used by medical personnel (e.g., EMTs in route to a hospital, at the hospital, or by physician during follow-up care) to access any available information about the incident.

Of course, the specific information that is conveyed as part of an emergency status message 500 may vary widely, with more, less or different information being transmitted as appropriate for any particular implementation. It should be appreciated that the amount of information broadcast as part of emergency status message 500 has to be tailored to the amount of data that can be transmitted as part of the Advertising Payload 466. Therefore, it is likely that the AED will have additional incident related information that would be of interest to a responding EMT. Since the BLE packet 450 includes the Broadcast Address 463, the EMT's listening device can establish a connection with the broadcasting AED. Once the responder's listening device is connected, the responder can retrieve other desired information, including, for example, recorded ECG samples via the connection.

The specific information that is made available through the connection can be varied in accordance with the system design goals. In some embodiments, authenticated users such as EMTs and other trained medical personnel may be given access to more information than untrained users that may connect to the AED. Such constraints may be based in part on factors such as the connected user's perceived level of expertise, HIPAA requirements, etc. In some embodiments, if the user is authenticated to a high enough level (e.g., a doctor or EMT), the user may even be permitted to transition the AED into a manual defibrillator mode in which the user can see real time information (such as the ECG readings) and is given control of more aspects of the shock deliver such as the shock delivery decisions and/or timing, capacitor charge levels, etc. Preferably this type of control would require a paired and authenticated connection.

In some embodiments, the instructional state and the incident related information may be broadcast independently as different advertisements. In such embodiments, the different advertisements can be broadcast over the same or different BLE advertising channels.

It some embodiments, the structure and/or contents of the payload may vary based on the information transmitted. For example, if the AED determines that a detected rhythm is not shockable (and no shocks have been administered), it may be desirable to provide more information about the diagnosis and there may be room to do so since no shock related information is required other than an indication that no shocks have been delivered. Thus, it should be appreciated that the information transmitted in any particular status message may vary widely based on the AED's operational state, use history and/or other relevant factors.

In some implementation, the communications unit is also capable of functioning as a beacon that transmits a message having a standardized beacon format such as an iBeacon or an Eddystone beacon. When BLE is used as the underlying short-range communications technology the beacon message is effectively a specially formatted BLE advertisement. A characteristic of these types of beacons is that many Smartphones and other devices are configured to handle beacon messages without requiring that an associated app be open at the time the message is received. Rather, an app developer can designate specific beacon handling code (e.g. a beacon handler) that can respond to specific predefined, registered beacon messages. When the Smartphone encounters such a beacon message, it will pass the beacon message to the beacon handling code of the associated app for appropriate handling. Thus, beacons can be used to notify an app with defibrillator support capabilities when it is within range of a defibrillator that is broadcasting beacon messages—regardless of whether the defibrillator support app is technically open at the time. This can be particularly helpful because many users may be disinclined or forget to keep their defibrillator support app open in the background which is required by many platforms to process advertisements targeted at an app or class of apps.

Figure 10:
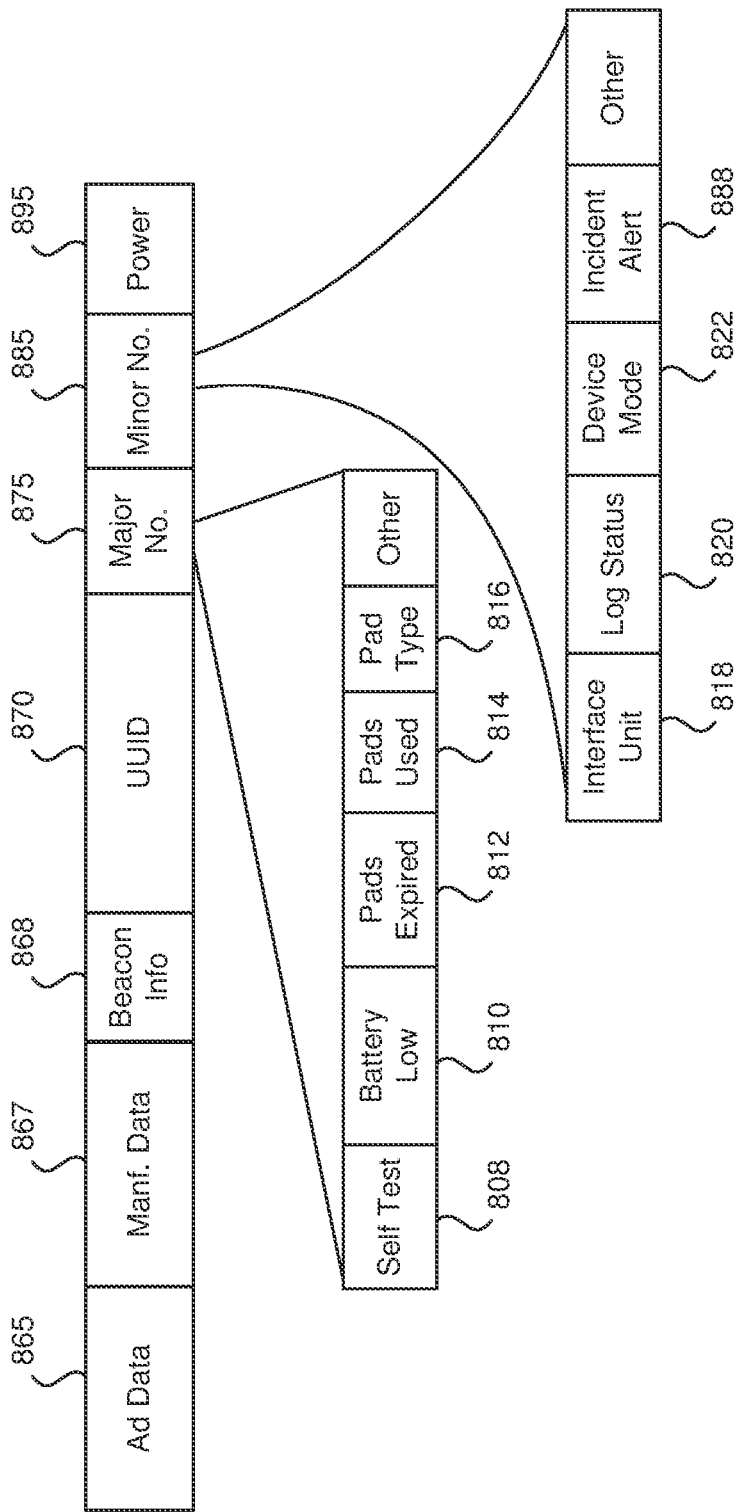
FIG. 10 is a flow chart illustrating the contents of a beacon in accordance with one embodiment.

FIG. 10 illustrates a BLE 4.0 compatible iBeacon advertising frame. The first three bytes, referred to as advertising data 865, are standard BLE flags. The next 4 bytes, referred to as Apple data 867, are Apple defined data that effectively defines the packet as an iBeacon (it is noted that this is frequently referred to as manufacture data in the context of the BLE spec, but it is important to understand that in this context the identified manufacturer is Apple, not the manufacture or administrator of the defibrillator). The following 2 bytes 868 define the beacon type and length. The next 16 bytes are required by the iBeacon specification to be an identifier field that contains a UUID 870. The UUID uniquely identifies the defibrillator and may be generated using any of a variety to techniques. In some embodiments, the UUID may be based at least in part on a manufacturer identifier and the defibrillator's serial number although this is not required.

The next two bytes are referred to in the iBeacon specification as a major value field 875 and the two bytes that follow the major number field 875 are referred to as a minor number field 885. In conventional iBeacon deployments the major and minor value pairs are used to segment and distinguish subspaces within a venue. However, that is not how those fields are used in the present disclosure. Rather, the characteristic that is relevant to the present disclosure is that these are values can be defined by the manufacture (or other entity) setting up the defibrillator's iBeacons. A power field 895 follows the minor number. The power field defines the transmitter power level.

In the described embodiment, the major and minor value fields 875 and 885 are used to transmit defibrillator status information and/or other information that is relevant to defibrillator management. The status information may include some or all of the status indicators in the standby status message structure described above with respect to FIG. 3A. For example, in a particular implementation, the major field 875 includes a self test flag 808, a battery low flag 810, a pad expired flag 812, a pads used flag 814, and a connected pad type indicator 816. The minor number may include an interface unit connected flag 818, a log status flag 820, a device mode indicator 822 and a nearby incident alert flag 888. Of course the specific status indicators employed may vary based on the needs of the system, and any of the flags may be implemented as other types of indicators and vice versa as desired. It should be appreciated that this is a very unique usage of a beacon in a manner that allows us to use an industry standard technologies (e.g. beacons) in a different way to convey status information from an AED to external devices.

Since the freely definable "payload" portion of the current iBeacon protocol is for the most part limited to the 4 bytes attributed to the major and minor numbers, the iBeacon doesn't have as much useable "payload" as a standard BLE 4.1 or 4.2 packet and it has much less freely definable payload than a standard BLE 5.0 or 5.1 packet. Eddystone beacons conceptually have more useable payloads than iBeacons. Specifically, the Eddystone Beacon includes a 20 byte long "Eddystone Frame," which is essentially a data frame. Eddystone Beacons can currently be configured to cycle through up to 4 distinct data frames. There are currently three defined Eddystone frame types but much like the iBeacon major and minor numbers, some of these data frames can be modified to convey defibrillator status information and/or other information that the defibrillator may wish to convey.

In view of the foregoing, it should be apparent that there are some advantages and disadvantages of using beacons and some advantages and disadvantages of using more traditional advertising packets. Therefore, in some embodiments, a defibrillator may be configured to broadcast both beacons and more traditional advertisements. The relative frequency at which the beacons and traditional advertisements are broadcast may be selected to meet the needs and design goals of any particular system. For example, in some embodiments when the defibrillator is in the standby mode, the communication unit may alternate back and forth between broadcasting a beacon status message and a standard BLE advertisement. Alternatively, beacons may be sent at one rate and standard advertisements at another rate and/or beacons may be interspersed at different frequencies in standard advertisements or vice versa. In some embodiments, beacons may be transmitted on a different advertising channel than the standard advertisements.

In various implementations, the beacon handling code can be designed to perform any or all of the advertisement handling functions described above or below. This can analyzing a received beacon and performing any appropriate actions in the background based thereon. The actions performed can vary widely as well. For example, the handling code can be configured to determine when a received advertising packet contains new information that should be forwarded to a management server and doing the same. It can also include tasks like automatically launching the defibrillator support app or prompting a user to launch the defibrillator support app if either of those actions are deemed appropriate based on information contained in the beacon.

Figure 14:
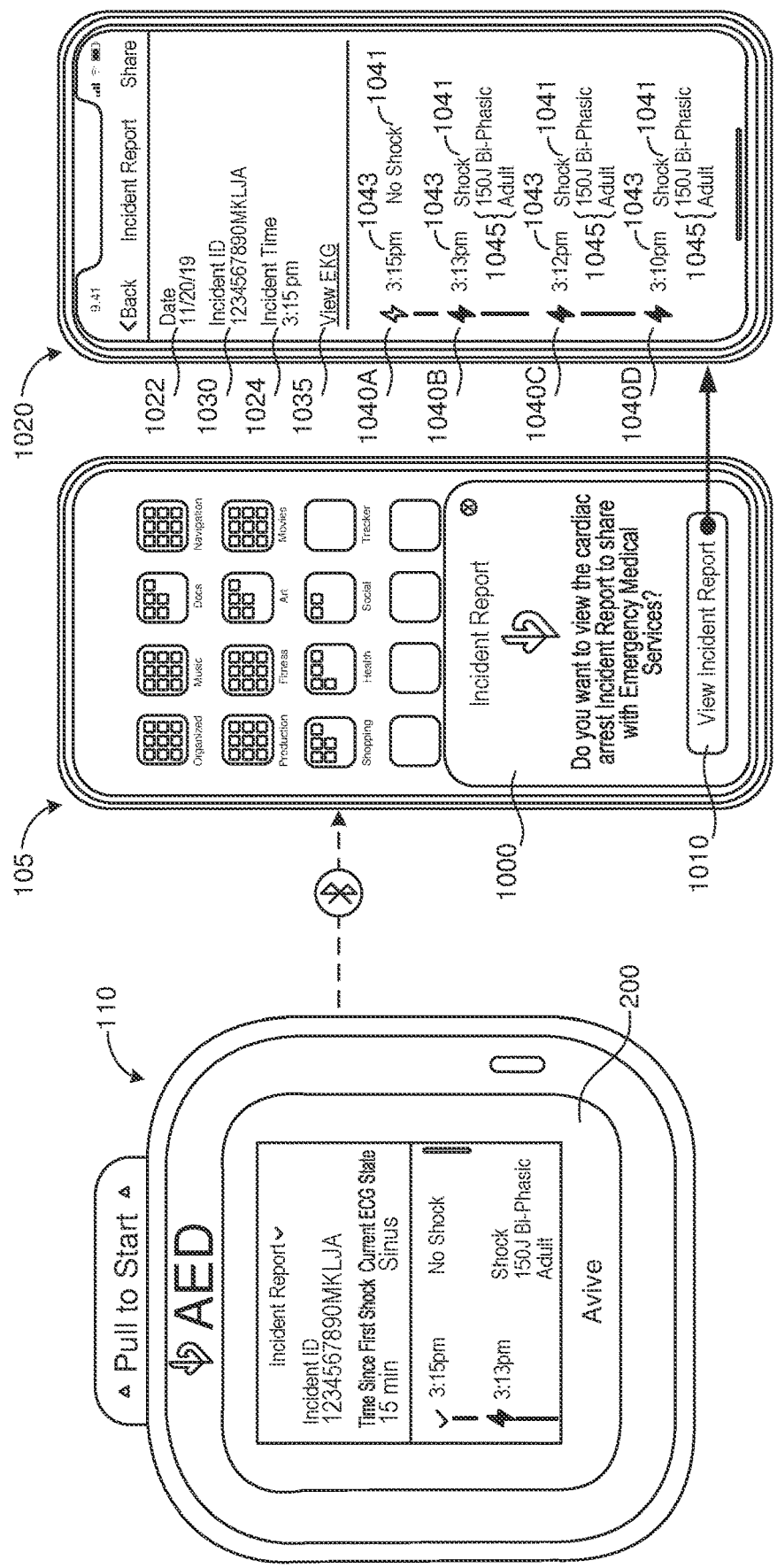
FIG. 14 is a diagram illustrating a representative Incident Report Notification and a representative Incident Report.

FIG. 14 shows some screen shots illustrating an example of a notification scheme that can be implemented using the described beacons and status messages. In the illustrated embodiment, an AED 110 periodically transmits a beacon (as for example the beacon 860 illustrated in FIG. 10) while operating in an emergency mode.

The Device Mode flag 822 in beacon 860 indicates that the AED is currently operating in the emergency mode. A nearby Smartphone 105 receives the beacon 860 and a beacon handler operating on the Smartphone analyzes the beacon message. When the Device Mode flag 822 indicates that the AED is operating in an emergency mode, the beacon handler causes the Smartphone to generate a user notification such as the Incident Report Notification 1000 shown in FIG. 10. In some implementations, the notification has the appearance of a notification generated by the host device (e.g., the operating system). In others, the notification may have the appearance of a notification initiated by an app.

The Incident Report Notification 1000 indicates that incident related information is available and includes a View Report button 1010 or other suitable GUI widget. User selection of the View Report button 1010 (or other suitable GUI widget) will open or otherwise activate the app associated with the beacon handler and the app will display an incident report 1020. As previously mentioned, the associated app may be a dedicated defibrillator support app, a more general health app (e.g., Apple Health or others) or take any other appropriate form.

In the illustrated embodiment, incident report 1020 displays incident related information that is available in the emergency status messages 800 illustrated in FIG. 5B or otherwise generally known to the app. This includes the current date 1022 and time 1024, an Incident ID 1030, and basic shock related information 1040. The current date 1022 and time 1024 may be known by the Smartphone. The Incident ID is received as part of the emergency status messages 800. For example, the Incident ID may be the concatenation of the device identifier 422 and the activation timestamp 846. The shock related information may include an indication of shock/no shock decisions made by the defibrillator, and if/when a shock is administered, the time the shock was administered and the nominal energy delivered by the shock as illustrated by 1040B, 1040C and 1040D. If the victim's heart rhythm is determined to be normal or otherwise non-shockable, the shock related information may simply be an indication that a no shock determination was made as illustrated by 1040A. The basic shock related information 1040 can be determined based on the identifiers in status message Shock Info fields 850 which present status information about shock related parameter. In the embodiment of FIG. 5B, these identifiers include the shock decision (shock/no shock) indicator, the child/adult indicator and the timestamp. For each reported shock decision, the shock/no shock indicator is used to indicate whether or the victim's heart rhythm was determined to be shockable or not as shown in shock decision field 1041. The timestamp in the Shock Info field is used to indicate the time that the shock was delivered or the reported no shock decision was made as shown in time filed 1043. The child/adult indicator is used to determine whether an adult shock or a pediatric shock was delivered as shown in shock field 1045. In some embodiments the Shock Info fields may include an indication of the shock energy delivered. If an indication of the shock energy delivered in included in the status messages, that value may be displayed in the shock filed 1045. However, that is often not required. Rather, the shock energy protocol used by the defibrillator may be predetermined and therefore known to the defibrillator support app so that the app may state the nominal shock energy delivered by simply knowing the defibrillator's shock energy delivery protocol. For example, in the illustrated embodiment, all adult shocks are delivered at an energy delivery level of 150 joules and this information is conveyed in shock field 1045. In other implementations, the energy delivered may increase in subsequent shocks—e.g., the first shock may be delivered at 150 joules, a second shock at 165 joules and third and subsequent shocks at 180 joules—or any other desired protocol may be used.

The Incident Report 1020 may also display other available information or include links to other information of interest, including information that may not be available in the status reports themselves. For example, in some embodiments, the Incident Report 1020 may include a View ECG button 1035 that facilitates the display of the victim's ECG in real time. Since the status messages do not include the live ECG, the Smartphone 105 would need to establish a connection with the defibrillator in order to display the ECG. Thus, in some embodiments, selection of the View ECG button causes the app to direct the Smartphone 105 to establish a wireless connection with the defibrillator or the user to establish a wired connection with the defibrillator. The real time ECG readings can then be delivered to the Smartphone for display in a different screen (not shown). Although the example of a View ECG button is provided, it should be appreciated that the Incident Report 1020 may include links to a variety of other functionalities that may be helpful to responders. When desired, some of the functionalities (such as the View ECG functionality) may only be made available to credentialed responders (e.g., emergency medical personnel and other professional responders). Such controls may be implemented by the controlling app (e.g., the defibrillator support app) which may provide different levels of information to different classes of responders.

Figure 6:
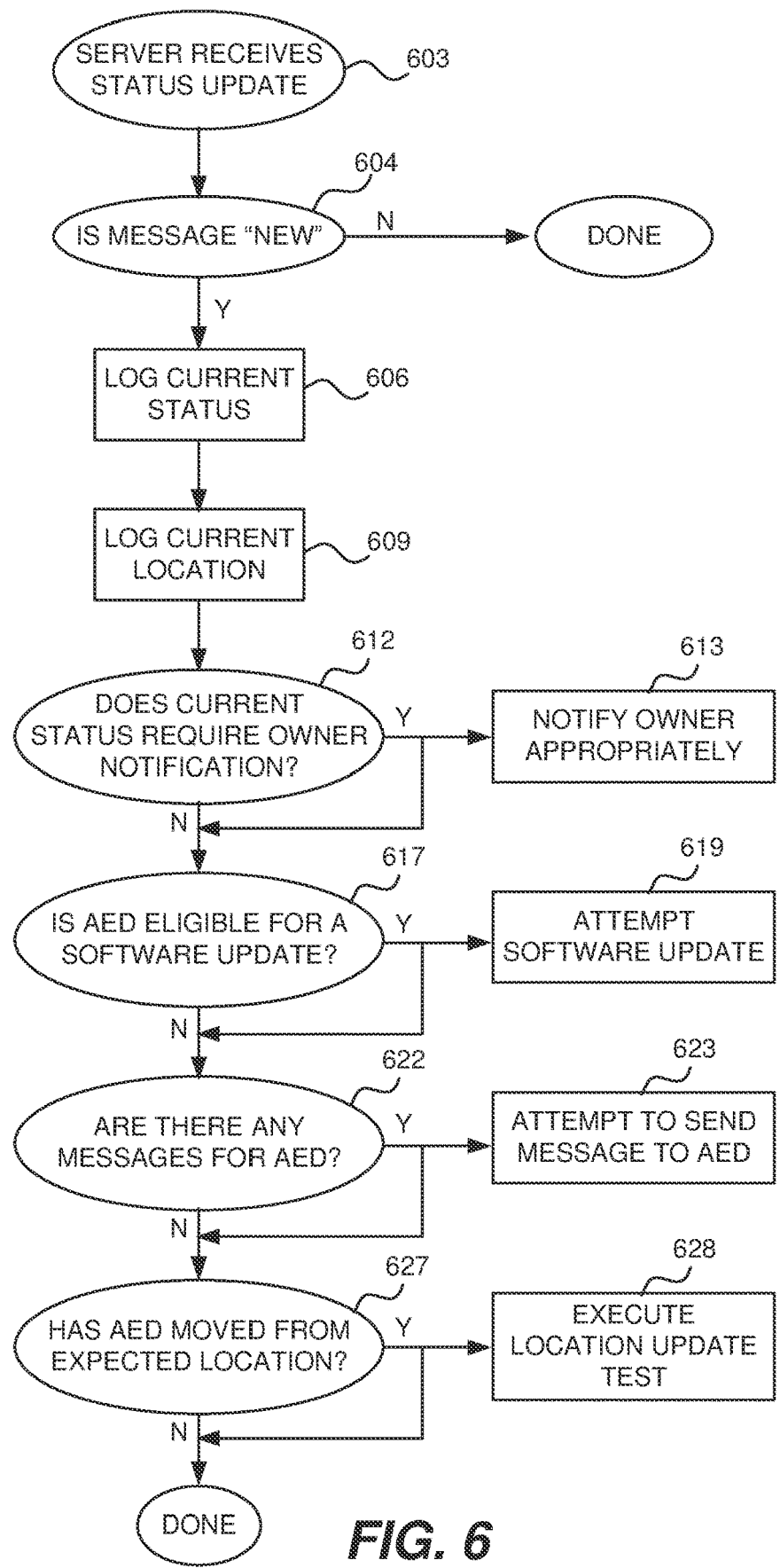
FIG. 6 is a flow chart illustrating a method of responding to standby status updates received by an AED management server.

When a standby status message 420 is passed to the AED management server 300, the server can handle the received information in any way deemed appropriate. FIG. 6 illustrates one way of handling the received status update.

When a new standby status update message 420 is received (block 603), the server checks the timestamp or message identifier and the unique device identifier 422 (e.g.

serial number) to determine whether the received status message is more recent than the currently stored version for the identified AED (block 604). If the received status update is new (the yes branch from block 604), the server logs the current status (block 606) and the perceived location (block 609) of the defibrillator. Since the status message 420 includes the transmitting device's serial number (or other unique identifier) 422, the received message can be associated with the particular AED that sent the message, regardless of the path that the message traveled to reach the server. Alternatively, if the server has already received and logged a more recent status message, or the same status message (e.g., from another source or earlier transmission), the message may effectively be ignored or noted for other only for tracking purposes—represented by the no branch from block 604.

In some circumstances, a received status message may indicate a problem that requires the owner/administer of the AED to be notified of an issue (as represented by block 612). Of course, the nature of the notification provided to the owner/administrator may vary widely based on the nature of the problem identified. For example, if the AED's internal battery is low (as indicated by battery level indicator 428) it may be desirable to send a message indicating that the battery is low and reminding the owner/administrator to charge or replace the AED's battery as appropriate. Similarly, if the electrode pads need replacement or other attention as indicated by electrode pad indicators 432, 434, or 436, a message may be sent to the owner indicating that the electrode pads need to be replaced or otherwise attended to. If the AED is not functional or has failed a status check, the owner may be informed that the AED is no longer operational and should be taken in for maintenance or replaced.

Figure 7:
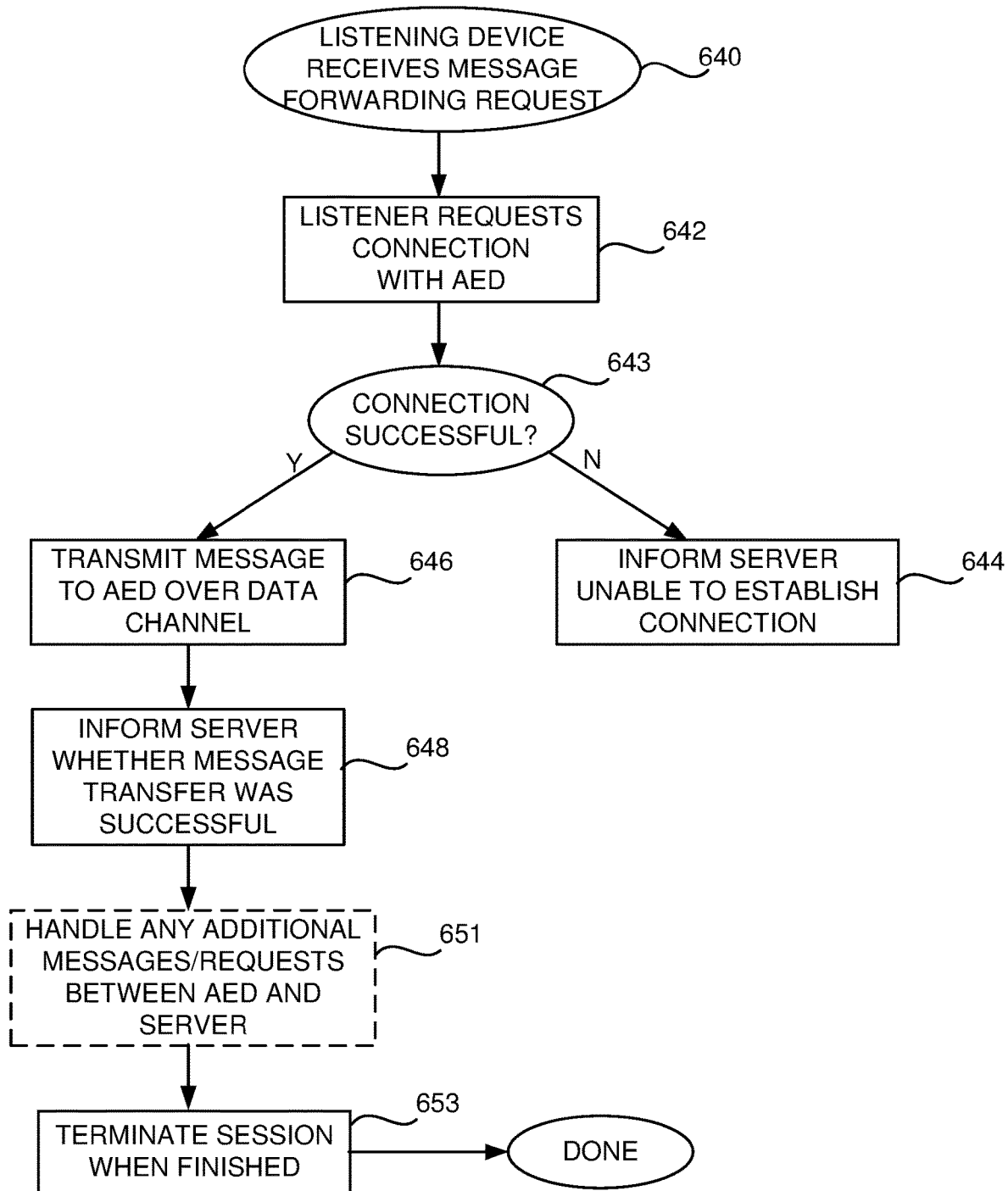
FIG. 7 is a flow chart illustrating a method of using an AED listener as an intermediary to forward information to the AED.

The server 300 may also check to see whether the AED's firmware or software is up to date as represented by block 617. If not, the server may attempt to deliver a software/firmware update to the AED as represented by block 619 or notify the owner of the need to update the software/firmware. In some embodiments, the software/firmware update can be delivered to the AED via the device that forwarded the status message to the server. For example, the server can deliver the latest version of the AED's software/firmware to the reporting listening device. The listener in turn, can establish a wireless connection with the AED (as discussed below with reference to FIG. 7) and deliver the software update over the wireless connection. In this manner, the software update can be delivered to the listening device via a variety of different types of intermediaries. In some circumstances, the intermediary can be a communication device (e.g. interface unit 200) that is attached to or otherwise uniquely associated with the AED. In others, the intermediary can be a mobile device (e.g. a cell phone, tablet or mobile communication device) associated with the AED's owner or administrator. In still other circumstances, the intermediary device may simply be an unaffiliated mobile device that has an appropriate defibrillator listener app installed thereon and happens to be in the vicinity of the AED for sufficient time to complete the software download.

The server may also check to see whether there are any messages for the AED as represented by block 622. If so, the server can attempt to deliver the message to the AED as represented by block 623. Virtually any type of message that is relevant to the AED can be delivered in this manner. For example, if the AED has incident information available (as indicated by the past incident data available identifier 445) the management server may send a query requesting that such information be uploaded to the server. In another example, if the management server determines that the status messages 420 are being broadcast too frequently or not often enough, the AED can be instructed to change the frequency of the status messages. In another example, the AED can be instructed to deactivate itself if it is subject to a recall or other action that requires its deactivation. In other examples, the AED could be instructed to initiate a self-test, flash a light, issue an audio message or any perform any other desired action.

When the server receives geo location information about the AED the server can also determine whether the AED has moved from its expected location as represented by block 627. If so, the server 300 can execute any location update tests that might be appropriate as represented by block 628. For example, when the AED is expected to remain in a single location, in might be desirable to inform the owner that the AED has been moved. Alternatively, if the AED is a public access AED whose location is identified on a public access AED map—it may be desirable to act appropriately for the map requirements. The appropriate actions may vary based on circumstances, but could include actions such as graying out or removing the AED from its previous shown location; marking the new location of the AED, etc. When handling such location changes it may be desirable to require some level of hysteresis (in the sense of receiving several different messages spaced over time that report the same location) before a new location for the AED is marked on the AED map.

A feature of Bluetooth Low Energy is that a Bluetooth enabled device is typically able to establish connections with (pair with) other nearby Bluetooth devices to facilitate two way communications and/or the transfer of larger amounts of data. These capabilities are also useful in the context of an AED and can be utilized in a variety of different scenarios.

In one example, an EMT or authorized emergency responder arriving on the scene of a cardiac incident may receive some basic information about the status of the incident through the emergency mode status messages 500. However, the AED will often have much more information about the incident than is seen in the broadcast data. For example, the additional incident information may include actual ECGs that have been detected, more complete information about the diagnoses made by the AED, and full information about any shocks delivered, including their respective timing, power level, etc. In some circumstances the AED may have other recorded information such as information about CPR chest compressions, the patient's blood oxygen levels, etc.

In some embodiments, an emergency responder on the scene can obtain access to this additional information by connecting with the AED via either a wired or a wireless connection. For example, an EMT may have an EMT defibrillator control app installed on a mobile device that provides more functionality than a standard defibrillator app. The EMT defibrillator control app can prompt the EMT to access additional incident information by initiating a BLE data connection with the AED. A connection can readily be established using standard Bluetooth connection protocols when both the AED and the EMT's mobile device are BLE enabled. In other embodiments, the EMT may make a wired connection between the AED and the EMT's mobile device to obtain the additional incident information.

In another example, a bystander that is not an emergency responder may wirelessly connect to the AED during early stages of an incident to facilitate forwarding any pertinent incident information to EMTs or other emergency responders that may be on their way to the incident. This enables the EMTs to have as much information as possible about the incident before they even arrive on the scene—which can help speed the EMTs' response when they arrive. Such incident information can be transmitted to responding ambulances, paramedics, etc. through existing networks such as the SIREN electronic medical records system and/or other suitable systems.

In still other embodiments, the wireless communications module may be configured as a non-connectable broadcaster when operating in an emergency operating mode. That is, the wireless communications module broadcasts status messages while operating in the emergency mode, but it will not allow wireless connections with external devices while operating in the emergency mode. In such embodiments, wired or other physical connections may optionally be permitted (or not permitted) during emergency mode operation. An advantage of making the Bluetooth module non-connectable during emergency use of the defibrillator is that it helps ensure that defibrillator resources aren't wasted managing Bluetooth connections and/or responding to requests from external devices during the incident.

Of course, a wide variety of different access rules can be implemented to define who can and/or who can't wirelessly connect to (pair with) an AED at different times. The access rules associated with any particular defibrillator may vary based on a variety of different factors, including, but not limited to, factors such as (1) the operating state of the defibrillator (e.g., whether the device is currently in an emergency mode, a standby mode, etc.); (2) the defibrillator's storage location (e.g., a public access AED stored in a public location such as a sports field or a building lobby may permit wider access than a personal AED stored at home; (3) the owner or operator's preferences; etc.

Connections can also be utilized to facilitate the delivery of messages from the management server 300 to the AED via a listener. One such method is described next with reference to FIG. 7. A variety of different types of messages can be delivered in this manner, including software updates. When the server determines that it wants to transmit information to the AED via the listener that it received a status message from, it sends the listener the information to be forwarded and a message forwarding request. After receiving the message forwarding request (as represented by block 640), the listener requests a wireless connection with the AED (block 642). When Bluetooth Low Energy is used as the underlying communication technology, the connection request can be a standard BLE connection request. If the listener is unable to establish a connection with the AED (decision block 643), the server 300 is so informed and the message is not passed to the AED (block 644). There are a number of reasons the listener may not be able to establish a connection. For example, when the listener is a mobile device, it may have been carried out of range of the AED. In another example, in some embodiments, the AED may not allow connections to be made when it is in emergency mode or has a battery charge level below a designated threshold.

If the listener is able to establish a connection (decision block 643), the message is transmitted to the AED over the connection (e.g., a Bluetooth data channel) (block 646). When the message transfer is successful, the intermediary device so informs the server (block 648). When a connection is established with the AED, the listening device is no longer acting as a listener. Rather it has a full connection with the AED. As such, the connected device can communicate as desired with the AED, and if requested, it can act as an intermediary facilitating communications back and forth between the server and the AED as represented by block 651. When the desired communications are completed, the session is terminated and the intermediate device reverts to it function as a listener as represented by block 653.

The described approach can be used to transfer any types of messages between the server and the AED. As previously mentioned one of the uses of this type of process is expected to be in the delivery of software updates for the AED. However, as previously mentioned, a variety of other types of messages and/or requests can be delivered this way as well.

Figure 11:
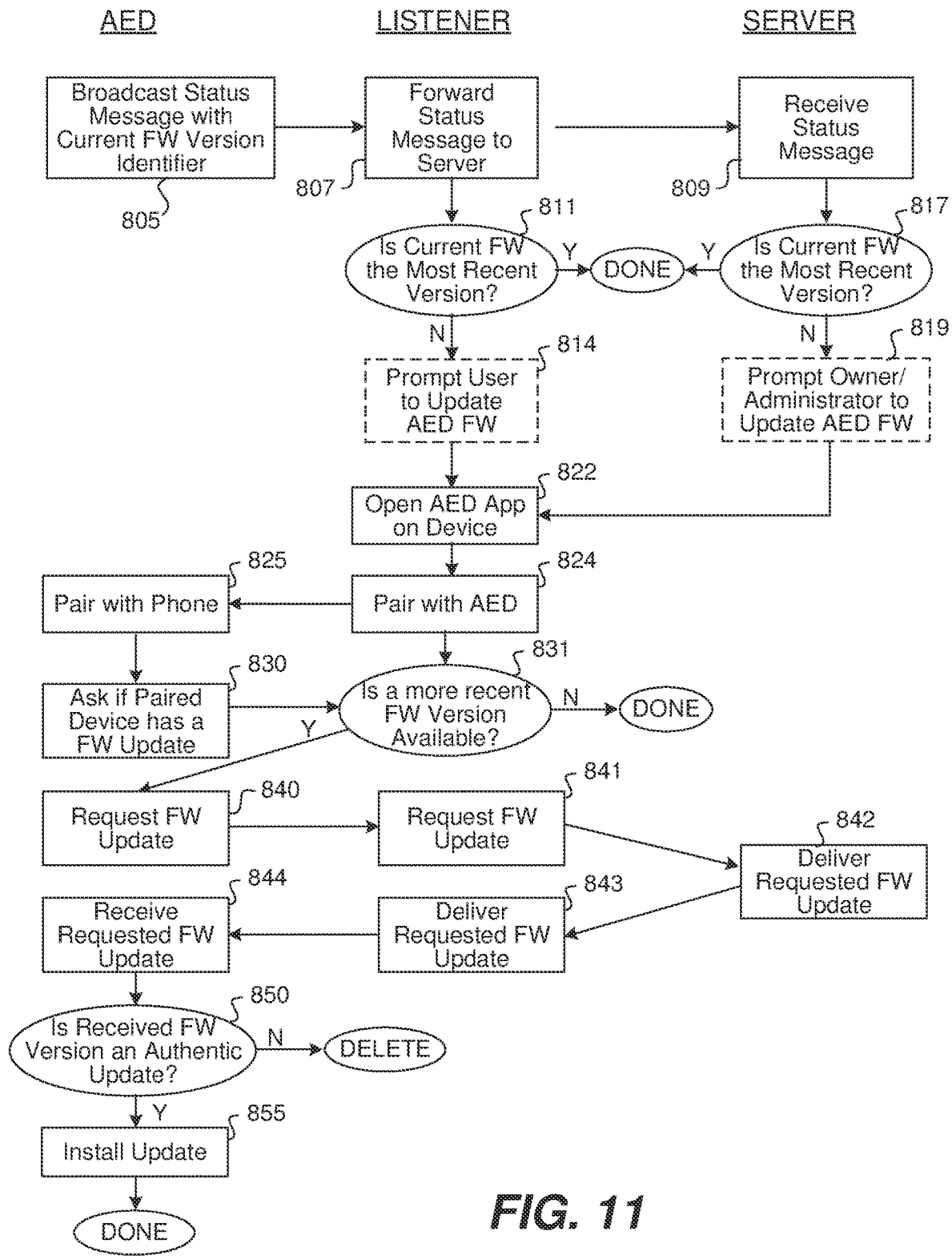
FIG. 11 is a flow chart illustrating a method of updating an AED's firmware via a listener that received a status message broadcast by the AED.

The advertising framework described above facilitates a variety of different communications strategies that working together can make it easier to track and manage AEDs in a variety of settings. To help illustrate this point, a few representative information flows will be described with reference to FIG. 11. FIG. 11 illustrates a few flows through which firmware updates can be delivered to an AED. However, it should be appreciated that the communications strategies employed for identifying the need for firmware updates and/or delivering such updates from a management server to an AED can be used to convey a wide variety of information to or from the AED.

As discussed above, the AED periodically broadcasts status messages, which may be either beacons or more other advertisements. (Block 805). Any given status messages may be received by one or more nearby listeners. In many cases, the listeners will be Smartphones or other mobile communication devices that have an app installed thereon that knows how to handle the status messages. The app can be a dedicated AED app provided by the defibrillator manufacture, a health related app associated with the Smartphone manufacturer or others, or any other app that is integrated with a defibrillator management system (e.g., with AED management server 300). Although it is expected that Smartphones and similar mobile devices will be the most commonly configured listeners, it should be appreciated that similar functionality can be incorporated into a variety of other Bluetooth (or other suitable wireless protocol) enabled devices including home networking hubs/components, IOT hubs/devices and/or a variety of other devices (e.g., Apple's Homepod, Amazon's Echo, Google's Home, Samsung's SmartThings hub, etc.).

When appropriate, the listener will forward a received status message to an appropriate server (e.g. AED management server 300) as previously discussed. Block 807. The status message may be forwarded directly from the listener to the management server, or indirectly through other components such as a home networking or virtual assistance network server.

Either or both the listener or the server may evaluate the status message to determine what, if any actions are appropriate. In the context of firmware updates, this may include checking the firmware version number 449 to determine whether it is the latest firmware version available for the AED. (Blocks 811, 817). When performed by the listener, the listener may have the latest version numbers stored therein and determine that the firmware may be out of date by simply comparing the received version number to the stored "most recent" version number, or it may ask the server for the latest version number, or ask whether the version identified in the forwarded status message is the latest number. If the AED is currently using the latest available firmware version (which is expected the vast majority of the time), nothing further needs to be done with respect to firmware updates. However, if the AED's current firmware is out of date, either the listener or the server, or both, may take actions to motivate or initiate a firmware update.

For example, if the listener determines that the firmware is out of date, it may prompt the user to update the AED's firmware. Alternatively, the server may ask the listener to generate such a prompt. The prompt can be a notification that a nearby AED needs it software updated and asks the user whether they would like to update that software at that time. Block 814. In some implementations, such notifications would only be generated on listener devices associated with an owner or administrator of the AED. However, that is not a requirement. Rather, if an interested volunteer has opted in, they could receive notifications from public AEDs that they are not personally responsible for if the owner/administrator opted in for such public updates. As will be described in more detail below, in some preferred implementations, the listener only acts as a conduit between the server and the AED for such updates, which helps ensure that such publicly delivered updates can be delivered in a reliably secure manner In other implementations, the updates can be transferred in the background when the listener has authorized background updates thereby potentially eliminating the need to generate a user prompt. These types of update are sometime referred to as passerby updates because they provide a mechanism through which firmware updates can be delivered to an AED without necessarily requiring an owner or administrator of an AED to make a special trip to the AED's location to facilitate the update. Of course, in many situations the "passerby" may actually be the AED's owner or administrator or a person affiliated therewith who happens to be in the vicinity of the AED.

In another use case, the server may determine that the firmware is out of date and send a message to the owner/administrator of the AED asking the owner/administrator to update the AED's firmware. (Block 819). The owner/administrator notifications are particularly desirable when passerby updates are not authorized or not successful for any reason.

At some point a prompted user (owner, administrator or passerby) may elect to update the AED's firmware. To accomplish this, the AED app executing on a listening device may be opened by the user if it is not already open. The app directs the listener to establish a wireless connection (e.g. a Bluetooth connection) with the AED which is often referred to as "pairing" with the AED. (Blocks 824, 825). The advertisements broadcast by the AED provide information suitable for initiating a Bluetooth connection with the AED in a conventional manner.

In some embodiments, the AED is configured so that it will not accept connection requests when it is operating in an emergency mode but will accept connections when it is not in an emergency operating mode.

In some embodiments, the AED is further configured such that after a connection is established, the AED can ask connected devices for information and receive responses thereto, but the AED will not accept or act on requests or commands received from connected devices. That is, all requests must originate from the AED and the AED will ignore any requests or commands received from the connected device. This architecture can greatly improve the AED's security. In this architecture, the AED may have no way of knowing whether a firmware update is available (or any other information if interest is available). When such an architecture is used, the AED may be configured to send a set of predefined requests to a connected device anytime a connection is established. These requests can effectively ask for all of the types of information that the listener or the server may potentially be interested in delivering to the AED. One of the predefined requests may be to ask the newly paired listener whether a more recent firmware version is available. (Block 830). The connected device may already know the answer to that question and respond accordingly. Alternatively, the connected device may pass the request to the server, which responds through the connected device.

When a new firmware version is confirmed to be available, the AED requests the update. Block 840. The firmware update request is received by the connected device and forwarded to the server, which replies to the connected device with the requested firmware update. The connected device, in turn, passes the update to the AED. Blocks 841-844.

After receiving the firmware update, the AED authenticates the received update. Block 850. If the update is successfully authenticated, it is installed and verified and validated. Block 855. The AED executes a self-test as part of the validation, and the self-test must be successful for the validation to succeed. If the update cannot be authenticated, it is deleted. Similarly, if the update cannot be validated, the defibrillator will revert to the last known good firmware version and the update will be deleted. A suitable update validation and installation process is described in Applicant's Provisional Application No. 62/895,071, which is incorporated herein by reference.

The Applicant is developing defibrillators and particularly AEDs that include a number of connectivity features and/or are well suited for use in conjunction with the described broadcast approaches. By way of example, U.S. Pat. Nos. 10,029,109, 10,112,054, and 10,071,256 and U.S. patent application Ser. Nos. 16/145,657; 16/146,096 and 16/146,743 (each of which is incorporated herein by reference) describe a few such devices.

As illustrated in FIG. 1, the core of the modular defibrillator system is a base defibrillation unit (base unit) 110. The base defibrillation unit 110 is a fully functional AED that is configured so that its functionality can be supplemented through the use of a mobile communication device 105 (such as a Smartphone, a tablet computer, etc.) having a defibrillator support app installed thereon, or by attaching an interface unit 200 to the base unit 110. In some embodiments, a charging pack or other supplemental power storage unit can be attached to the base defibrillation unit to recharge a battery on the base unit, as appropriate, thereby effectively extending the base unit's usable life without an outside charge or battery replacement.

Figure 8:
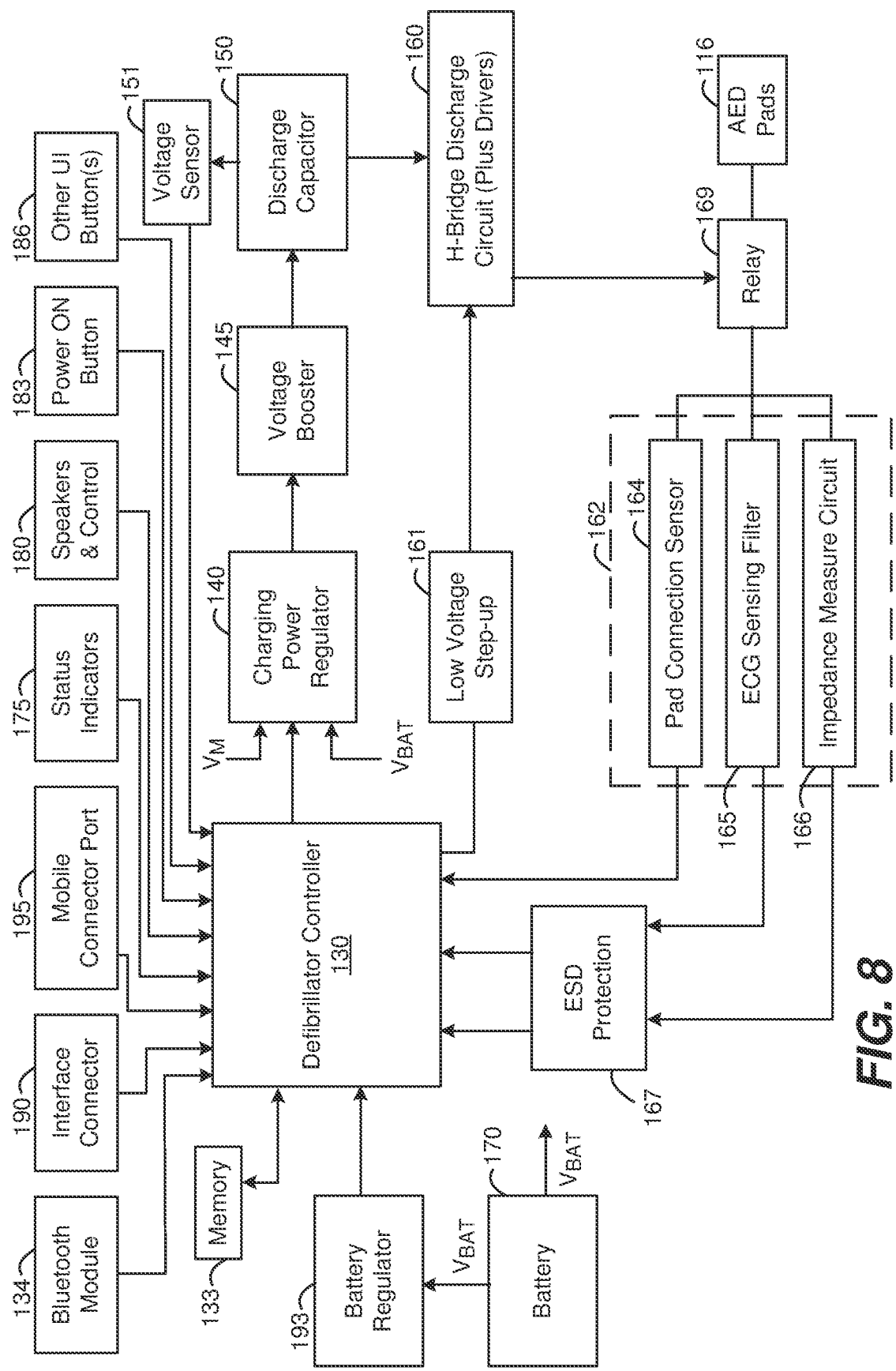
FIG. 8 is a block diagram illustrating electrical components of an embodiment of an AED.

FIG. 8 is a block diagram illustrating one representative electronics control architecture and associated components suitable for use in the base defibrillator unit 110. In the illustrated embodiment, the electronic components include a defibrillator controller 130, memory 133, a wireless communications module in the form of Bluetooth module 134, a charging power regulator 140, a voltage booster 145 (which may have multiple stages), a high voltage capacitor 150 for temporarily storing sufficient electrical energy suitable to provide a defibrillation shock, discharge control circuitry 160, pad related sensing circuitry 162 and relays 169, power storage unit 170, battery regulator 193, status indicator(s) 175, speaker(s) 180 and one or more electrical connectors (e.g., interface connector 190, mobile connector port 195, charger connector (not shown), etc). The charging power regulator 140 and voltage booster 145 which cooperate to control the charging of the shock discharge capacitor 150 are sometimes referred to herein as a charging circuit.

The defibrillator controller 130 is configured to control the operation of the base defibrillator unit and to direct communications with external devices, as appropriate. In some embodiments, the defibrillator controller includes a processor arranged to execute software or firmware having programmed instructions for controlling the operation of the base unit, directing interactions with a user and communications with external components.

The Bluetooth module 134 supports BLE communications and broadcasts status message advertisements as described above at the direction of Defibrillator controller 130.

The base defibrillator unit 110 may optionally be configured so that it is capable of drawing power from certain other available power sources beyond power storage unit 170 to expedite the charging of shock discharge capacitor 150. The charging power regulator 140 is configured to manage the current draws that supply the voltage booster, regardless of where that power may originate from. For example, in some embodiments, supplemental power may be supplied from a mobile device coupled to mobile connector port 195 or from a portable charger/supplemental battery pack coupled to charger connector 197.

The voltage booster 145 is arranged to boost the voltage from the operational voltage of power storage unit 170 to the desired operational voltage of the discharge capacitor 150, which in the described embodiment may be on the order of approximately 1400V-2000V (although the defibrillator may be designed to attain any desired voltage). In some embodiments, the boost is accomplished in a single stage, whereas in other embodiments, a multi stage boost converter is used. A few representative boost converters are described in the incorporated U.S. Pat. No. 10,029,109. By way of example, in some embodiments, a flyback converter, as for example, a valley switching flyback converter may be used as the voltage booster 145—although it should be appreciated that in other embodiments, a wide variety of other types of voltage boosters can be used.

A voltage sensor 151 is provided to read the voltage of the capacitor 150. The voltage sensor 151 may take the form of a voltage divider or any other suitable form. This capacitor voltage reading is utilized to determine when the shock discharge capacitor 150 is charged suitably for use. The sensed voltage is provided to controller 130 which determines when the capacitor 150 is charged sufficiently to deliver a defibrillation shock. The capacitor 150 can be charged to any desired level. This can be useful because different defibrillation protocols advise different voltage and/or energy level shocks for different conditions. Furthermore, if the initial shock is not sufficient to restart a normal cardiac rhythm, some recommended treatment protocols call for the use of progressively higher energy impulses in subsequently administered shocks (up to a point).

The discharge circuitry 160 may take a wide variety of different forms. In some embodiments, the discharge circuitry 160 includes an H-bridge along with the drivers that drive the H-bridge switches. The drivers are directed by defibrillator controller 130. The H-bridge outputs a biphasic (or other multi-phasic) shock to patient electrode pads 116 through relays 169. The relays 169 are configured to switch between an ECG detection mode in which the patient electrode pads 116 are coupled to the pad related sensing circuitry 162, and a shock delivery mode in which the patient electrode pads 116 are connected to H-Bridge to facilitate delivery of a defibrillation shock to the patient. Although specific components are described, it should be appreciated that their respective functionalities may be provided by a variety of other circuits.

The pad related sensing circuitry 162 may include a variety of different functions. By way of example, this may optionally include a pad connection sensor 164, ECG sensing/filtering circuitry 165 and impedance measurement filter 166. The pad connection sensor is arranged to detect the pads are actually connected to (plugged into) the base defibrillator unit 110. The ECG sensing/filtering circuitry 165 senses electrical activity of the patient's heart when the pads are attached to a patient. The filtered signal is then passed to defibrillator controller 130 for analysis to determine whether the detected cardiac rhythm indicates a condition that is a candidate to be treated by the administration of an electrical shock (i.e., whether the rhythm is a shockable rhythm) and the nature of the recommended shock. When a shockable rhythm is detected, the controller 130 directs the user appropriately and controls the shock delivery by directing the H-bridge drivers appropriately.

In some embodiments, the power storage unit 170 takes the form of one or more batteries such as rechargeable Lithium based batteries including Lithium-ion and other Lithium based chemistries, although other power storage devices such as one or more supercapacitors, ultracapacitors, etc. and/or other battery chemistries and/or combinations thereof may be used as deemed appropriate for any particular application. The power storage unit 170 is preferably rechargeable and may be recharged via any of a variety of charging mechanism. In some embodiments, the power storage unit 170 takes the form of a rechargeable battery. For convenience and simplicity, in much of the description below, we refer to the power storage unit 170 as a rechargeable battery. However, it should be appreciated that other types of power storage devices can readily be substituted for the battery. Also, the singular term "battery" is often used and it should be appreciated that the battery may be a unit composed of a single battery or a plurality of individual batteries and/or may comprise one or more other power storage components and/or combinations of different power storage units.

In some embodiments, the base defibrillator unit 110 is capable of drawing power from other available power sources for the purpose of one or both of (a) expediting the charging of shock discharge capacitor 150 and (b) recharging the power storage unit 170. In some embodiments, the battery can be recharged using one or more of the externally accessible connector port 195, a dedicated charging station, a supplemental battery pack (portable charger), an interface unit 200, etc. as will be described in more detail below. When wireless charging is supported, the base defibrillator unit may include a wireless charging module 174 configured to facilitate inductive charging of the power storage unit 170 (e.g. using an inductive charging station 294, or other devices that support inductive charging, as for example an inductively charging battery pack, a cell phone with inductive charging capabilities, etc.).

The base unit also includes a number of software or firmware control algorithms installed in memory 133 and executable on the defibrillator controller. The control algorithms have programmed instructions suitable for controlling operation of the base unit and for coordinating the described broadcasts, as well as any point-to-point communications between the base unit 110 and the interface unit 200, connected devices 105, and/or any other attached or connected (wirelessly or wired) devices. These control routines include (but are not limited to): communication control algorithms, heart rhythm classification algorithms suitable for identifying shockable rhythms; capacitor charge management algorithms for managing the charging of the discharge capacitor; capacitor discharge management algorithms for managing the delivery of a shock as necessary; user interface management algorithms for managing the user instructions given by the defibrillator and/or any connected user interface devices (e.g. interface unit 200, mobile communication device 105) during an emergency; battery charge control algorithms for managing the charging of power storage unit 170; testing and reporting algorithms for managing and reporting self-testing of the base unit; software update control algorithms and verification files that facilitate software updates and the verification of the same.

In many installations, an AED will be expected to be stored for long periods of time without being plugged into power and therefore relying solely on battery power. Accordingly, it is important to minimize the power drain as much as possible during this time. In some embodiments, the defibrillator controller is configured to shut down power to all electrical components (including itself) except for (a) a real time clock (not shown), (b) the Bluetooth module 134, and (c) a power controller (not shown) when the AED is in the standby (resting) mode. In some embodiments, the clock and/or the power controller are integrated into the Bluetooth module 134 or an I/O adaptor board that includes the Bluetooth module. The clock is configured to periodically send a status check alarm to the power controller which wakes the power controller up from a sleep mode when the power controller is separate from the Bluetooth module. In response to the status check alarm, the power controller restores power to the entire system. Once power is restored, the defibrillator controller 130 performs a status check and instructs the Bluetooth module 134 to update the standby status message 420 as appropriate. After the status check is performed, the defibrillator controller will again shut down power to all electrical components except the clock, the Bluetooth module 134 and the power controller. The status check alarms can be generated at any desired intervals, as for example, once each day.

With the described power management scheme, the Bluetooth module 134 can continue to broadcast standby status messages even when the AED is powered down.

If the Bluetooth Module 134 makes a connection while the AED is in the standby mode, it sends a message to the power controller, which in turn, powers on the system, thereby allowing the defibrillator controller or other suitable component to communicate with the connecting device. Thus, the AED can effectively be woken up via a Bluetooth connection request. Of course, the power controller is also configured to power the system when a user presses the AED's "ON" button or otherwise activates the AED.

In other embodiments, one or more of the electrical components of the AED, such as the defibrillator controller 130, can be placed in a "sleep" mode rather than being turned off when the AED is in the standby mode. However, a significant advantage of actually turning the defibrillator controller and the bulk of the AED's electrical components off as opposed to placing them in a sleep mode is that it eliminates the power draw associated with the sleep mode, thereby potentially extending the AED's shelf life. It should be appreciated that the power controller/power down approach can be also used with AEDs that don't incorporate a Bluetooth module and/or support the low energy broadcasts described herein.

When a listener with a defibrillator support app installed thereon receives an emergency mode status message 500, the listener can display graphic instructions to a user that match the instructions issued from the AED base unit (e.g. an audio instruction issued by the AED, although the AED may issue instructions in other formats as well). As the AED gives different instructions to the user, the graphic instructions displayed on the listener (e.g., mobile communications device 105, interface unit 200, etc.) change to match the instructions from the AED.

The synchronization between the AED and the listener can be accomplished using a variety of different approaches. By way of example, one suitable approach is described with reference to the flow chart of FIG. 9. In the illustrated embodiment, the AED periodically broadcasts status messages during emergency use of the AED.

The specific intervals used may vary but they are preferably fairly frequent. By way of example, frequencies on the order of several status messages per second works well (e.g. 3-20 Hz). In one specific example, status messages are sent every 0.1 seconds (i.e., at a frequency of 10 Hz). When the AED issues its instructions as audio instructions, new graphic displays are preferably well synchronized with the corresponding audio instructions and the status message interval is selected to be short enough so that the graphic instructions do not lag noticeably behind any audio instructions that may be given to provide a positive user experience.

The listener receives this status message and uses the instruction state identifier 504 to determine which graphic to display. More specifically, in some embodiments, the defibrillator support app executing on the listener has a stored library/dictionary/database which pairs the instruction states received from the AED with specific graphics or graphic states of the listener. This helps ensure that the listener provides the correct graphic instruction. When the listener receives the status message from the AED, the listener checks its database to determine what graphic instruction (if any) corresponds to the current state of the defibrillator and should therefore be displayed. When a corresponding graphic instruction is found, the listener's processor directs its display screen to display that corresponding graphic.

It should be appreciated that more complex algorithms/methods may be implemented to account for outliers/false signals in the data stream. For example, if a listener received a false/incorrect status message that was corrupted in transit from the AED, instead of immediately displaying the new corresponding (incorrect) graphic, it may require multiple status messages to be received to re-affirm that it has received the correct uncorrupted information from the AED.

In some cases it may be beneficial for the listener to know ahead of time what instruction the AED plans to provide to the user. This can be helpful because some display screens may have a delay associated with displaying new graphics. To accommodate such planning, the status message may also include a next instruction indicator, as well as an indicator of the timing at which such an instruction will be generated. In embodiments that transmit the current state—the next instruction indicator can take the form of an indication of the next expected state. By receiving an indication of the AED's next instruction, the listener can prepare ahead of time for displaying the next corresponding graphic.

Another noteworthy feature of supplemental graphics management relates to the handling of a disconnection and/or poor connections during an emergency. In some embodiments, if the listener stops receiving status messages 500 for a period the listener will transition to a backup mode in which it no longer seeks to display graphics that are synchronized with any instructions issued by the AED.

The specific graphics and/or instructions displayed in the backup mode may vary based on design goals. For example, in one embodiment in which the display is relatively large, the listener reverts back to a single screen that displays all the instructions for use of the defibrillator in an ordered set of instructions. Such a display may be textual and/or graphic instructions. In another embodiment, the backup mode may be configured to allow the user to manually navigate through the graphic instructions; for instance, using front and back arrows. In another embodiment the screen may display text or graphics that indicate poor connection and that the user should follow the audio instructions of the AED. Of course, a variety of other specific graphics and/or instructions may be provided in other implementations.

Figure 9:
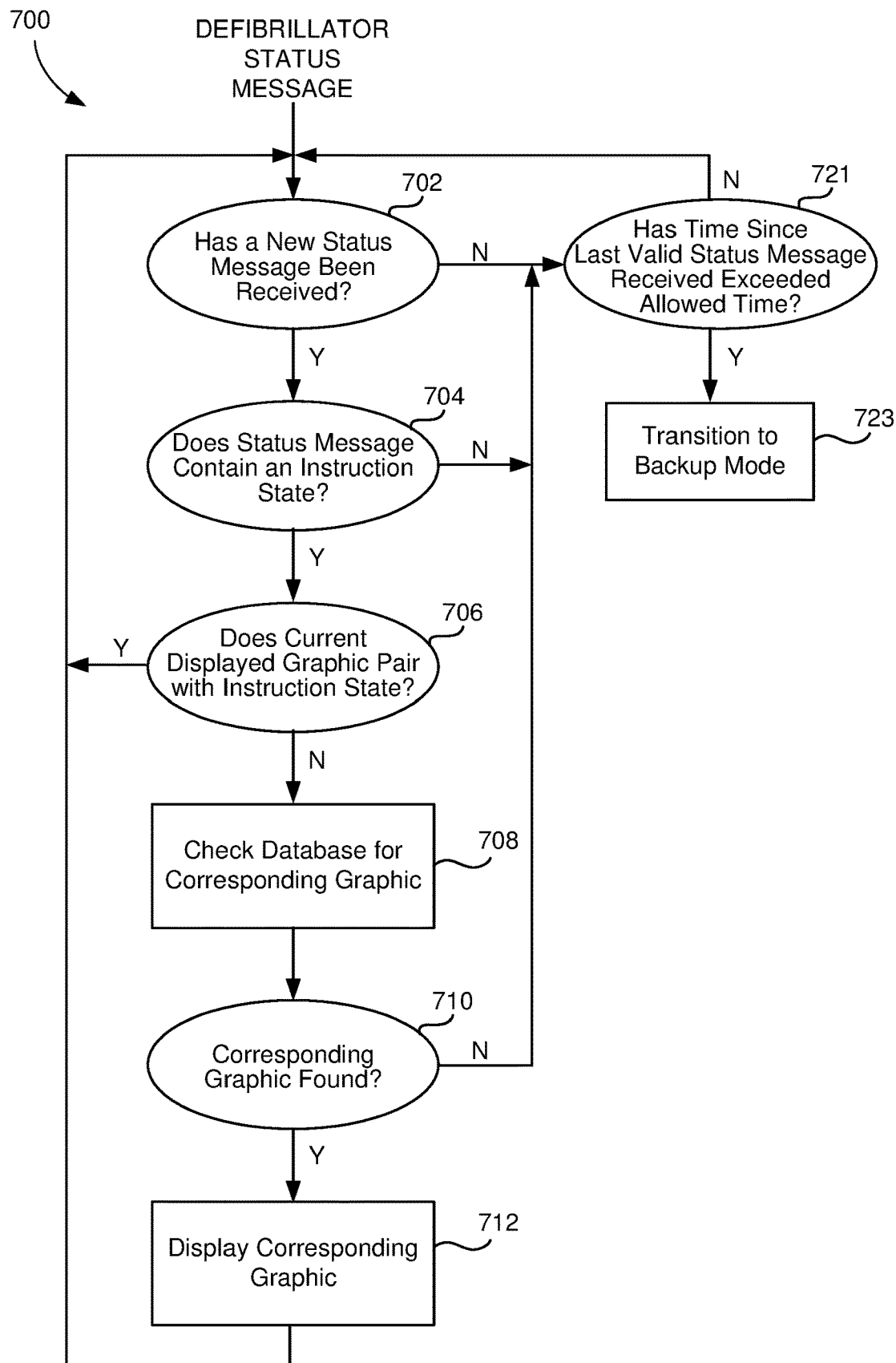
FIG. 9 is a flow chart illustrating a process for synchronizing graphics displayed on a listener with audio user instructions issued by an AED in accordance with one embodiment.

Referring next to FIG. 9, a representative in-sync graphics management process 700 will be described. As described above, the AED is configured to periodically broadcast status messages 500 during emergency use. Thus, each listener will periodically receive status messages from the AED. When a status message is received (as represented by the "Yes" branch from check 702), the logic determines whether the status message contains an instruction state as represented by check 704. If so, the logic determines whether the currently displayed graphic corresponds to the newly received instruction state as represented by check 706. If so, the current display is maintained and the logic waits for the next status message as represented by the "Yes" branch from check 706. Alternatively, if the current graphic does not match the instruction in check 706, the logic checks a database to find a corresponding graphic as represented by block 708. If a corresponding graphic is found as represented by the "Yes" branch from check 710, that "new" graphic is displayed as represented by block 712. Thereafter, the logic looks to receive the next status message.

As suggested above, in many implementations, the AED is expected to send updated status messages on a regular basis. If a status message isn't received as expected (as represented by the "No" branch from check 702), a check 721 is made to determine whether the time since the last valid message was received exceeds a designated timeout period. This may be achieved by examining the time since the last status message was received from the AED. If a set amount of time passes (e.g. 1 second, 0.5 sec, 0.1 sec, etc.) without receiving a status message from the AED, then the listener infers that it is not reliably tracking the AED's progress, and resorts to a backup mode as represented by block 723. If the backup mode is entered, appropriate backup graphics are displayed as previously discussed. Alternatively, if the allowable time period has not been exceeded, the logic awaits the next incoming status message as represented by the "no" branch from check 721. In the illustrated embodiment, the timeout period is longer than the expected status message reception interval. Although this is not a strict requirement, such an approach provides a system that is robust enough to handle occasionally dropped or corrupted packets.

It should be appreciated that a tracking loss may also be inferred using other metrics, such as the reception of corrupted status messages, un-readable data, or a nonsensical series of instructions. Thus, if a received status message does not contain a readable instruction state (as represented by the "no" branch from check 704) or no graphic is found that corresponds to a received instruction state (as represented by the "no" branch from check 710), the in-synch timeout logic can treat those events as non-reception of a new instruction in the timeout check 721. Thus, in some embodiments a last valid message received time used in timeout check 721 is only updated after validation of a received instruction state in a status message. By way of example, such validation may be based on confirmations from checks 706 or 712 or in other suitable manners.

Figure 12:
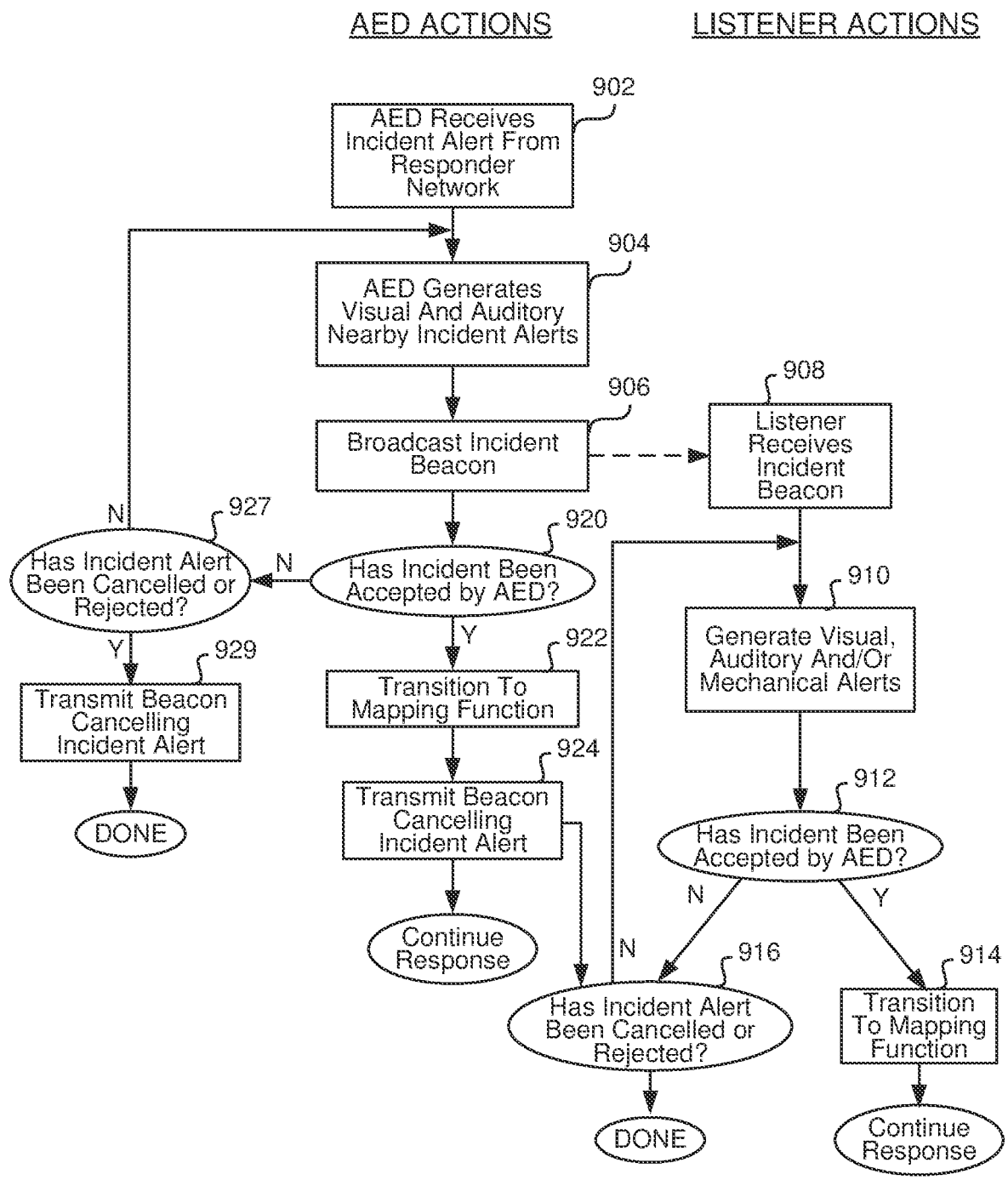
FIG. 12 is a flow chart illustrating a method of using beacons to extend the range of nearby incident alerts.

The use cases discussed above describe a variety of uses of advertisements and beacons. Another, quite different use of beacons (or other advertisements) is described next referring next to FIG. 12. In recent years, public responder networks have been proposed and/or developed which seek to notify volunteer responders that happen to be nearby a life threatening incident. The basic premise of public responder networks is that a citizen responder may be able to reach an incident (e.g., a cardiac arrest incident) more quickly than conventional emergency medical service. This is particularly critical for cardiac arrest incidents where statistics shown that survival rates decrease at a rate of on the order of 10% with each passing minute. In U.S. application Ser. No. 16/462,864 (which is incorporated herein by references), Applicant describes some novel public responder network frameworks and architectures. In some of the described embodiments, incident notifications are sent to AEDs that are located close to a reported incident. FIG. 12 begins at block 902 when such an incident alert is received. Typically, the incident alert would be received from a responder network server, although it can be triggered in other ways as well.

Upon receiving an incident alert, the notified AED issues an auditory and/or visual alert in an effort to catch the attention of persons that happen to be nearby the AED. Block 904. The alerts inform potential responders that there is a potential cardiac arrest incident nearby for which the AED may be useful and typically ask if a bystander can take the AED to the scene of the incident. By way of example, the AED may display a message on a display screen associated with the AED stating that there is an emergency incident nearby and asking potential users if they would be willing to take the AED to the location of the incident. The message displayed on the AED may also include a GUI widget that a user can select to indicate their willingness to help—which is treated as "accepting" the incident.

In parallel, incident beacons (and/or other incident advertisements) are broadcast by the AED. Block 906. In some embodiments, the beacon may be a status type beacon as described above with respect to FIG. 10 that further includes an incident alert identifier that indicates when the AED has transitioned to a nearby incident alert mode. Such an incident alert identifier can take the form of a flag or other indicator. In other embodiments, the incident alert may have a different structure that eliminates some or all of the other status information and only conveys information relevant to the alert.

In some embodiments, the AED sends incident relevant information as part of the incident beacon. This may include information such as the location of the incident (e.g., the GPS location) and/or an incident identifier. Additionally, in some embodiments, the incident beacon may also include the location of the AED itself. Of course, other relevant information may be provided as well. The location of the incident and the incident identifier would typically be received from the responder network, whereas the AED or a location module associated therewith would typically provide the AED location. The incident beacons may utilize any suitable beacon format. By way of example, iBeacons and Eddystone beacon are quite suitable.

The AED will continue to generate the nearby incident alert and broadcast the incident beacon until the incident has either been accepted by a responder on the AED itself or the incident alert has been canceled or rejected by another mechanism. Any suitably configured listeners that are close enough to receive the incident beacon (block 908) generate a corresponding notification on the listening device. (Block 910). The listener notification may have auditory, visual and/or mechanical components. For example, a Smartphone listener may display a nearby incident notification on the phone's display screen and generate a combination of sounds and/or vibration to attack the user's attention to the screen. The listener notification may include a GUI widget that a user can select to indicate their willingness to help— which is treated as "accepting" the incident. Of course other notification schemes and content are possible as well. The listener then determines whether the alert has been accepted. Block 912. If so, the listener transitions to a response function. A responder's acceptance of the incident may launch a defibrillator response App (if it is not already open) and the listener may transition to a mapping function that shows the location of the broadcasting AED and optionally the location of the victim. Block 914. The location of the broadcasting AED is given so that the responder can go pick up the AED. The location of the victim is given so that the responder can take the AED to the incident. In other embodiments, the responder may only be shown the location of the AED, which in turn would show the location of the incident. In still other embodiments the user may be expected to know the location of the broadcasting AED. Regardless, the listener then respond to the incident as appropriate for the given responder network.

The listener may continue to generate the alert until the incident has been accepted, cancelled or rejected. Block 916. The incident alert may be cancelled by the AED by sending an updated incident beacon that indicates that the alert has been cancelled. The cancellation can be due to someone else accepting the incident on the AED, due to the cancellation of the alert by the responder network (which may occur, for instance when emergency responders are confirmed to have arrived on the scene) or due to other appropriate triggers or timeouts. The listener alert may be cancelled by the listener if the user declines the alert or in response to other appropriate triggers or timeouts.

Returning to the perspective of the AED, if a bystander picks up the AED and accepts the incident (decision block 920), the AED with respond in accordance with a designated response protocol. This may include transitioning to a mapping function (block 922) to show the volunteer the location of the incident as described in the incorporated '864 application. Additionally, the AED will transmit a beacon that effectively cancels the incident alert. Block 924. The incident alert may be cancelled by sending an updated incident beacon that indicates that the alert has been cancelled. For example, if the incident beacon contains an incident alert flag, the flag can simply be set to "off" (i.e., no incident alert). Of course, a wide variety of other indicators can be used to cancel the incident alert in alternative embodiments. Any listeners that are generating a nearby incident notification will then cancel the notification.

The incident alert may be canceled for other reasons as well. For example, the incident alert may be cancelled by the responder network (which may occur, for instance when emergency responders are confirmed to have arrived on the scene) or due to other appropriate triggers or timeouts. Additionally, a person interacting with the AED may affirmatively reject the incident. Block 927. If the incident alert has been cancelled for any of these reasons, the AED will transmit an updated beacon that cancels the alert. Block 929.

Figure 13:
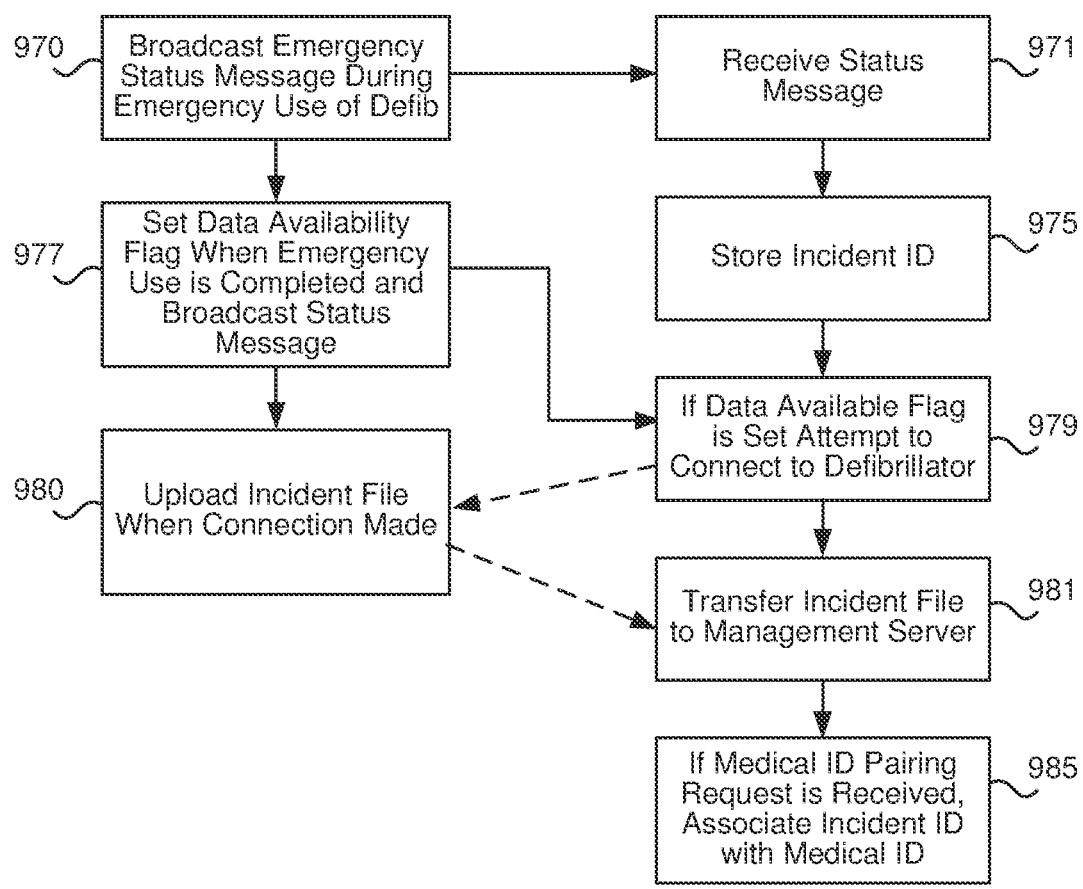
FIG. 13 is a flow chart illustrating a method of using Incident IDs.

Referring next to FIG. 13, some specific use cases that make use of the Incident IDs will be described. As previously mentioned, in some embodiments, the emergency status message includes a unique Incident Identifier (Incident ID). The Incident ID can be provided in a separate Incident ID field (not shown) or it may be composed of some of the other fields previously discussed. For example, in the embodiment of FIG. 5(*b*), the Incident ID may be the concatenation of the device identifier 422 and the activation timestamp 846 which together provides an identifier that is guaranteed to be unique. The Incident ID can be used by medical personnel (e.g., EMTs in route to a hospital, at the hospital, or by physician during follow-up care) to access any available information about the incident. For context, during an emergency, the base defibrillator unit 110 will typically record and/or log a lot of information about the incident. This may include things such as: (1) the actual ECGs sensed by the electrode pads; (2) the classification made for each analyzed heart rhythm segment—e.g., shock/ no shock, or a more detailed classification such as ventricular tachycardia; (3) details about any shock delivered; (4) the time the defibrillator was turned on; (5) user inputs made to the defibrillator (e.g., a user selection of a child or language button, etc.); (6) each event state (including but not limited to instruction state) that the defibrillator sequenced through during the incident and the time such state was entered; and/or (7) a variety of other information. The shock details may include information such as: (a) the time the shock was delivered; (b) the defibrillation shock voltage applied; (c) before and after heart rhythm segments; (d) sensed impedance; (e) peak current or other defibrillation waveform parameters; and/or (f) a variety of other information. Much of this information can be useful to doctors and other treating medical personnel. Other information may be useful to the defibrillator manufacturer in evaluating the defibrillator's use and operation during an emergency.

After a defibrillator has been used in an emergency incident, the incident information (which includes the Incident ID) will be uploaded to the management server 300. The Incident ID provides a mechanism by which medical personnel can retrieve the incident data. Broadcasting the Incident ID as part of the emergency status message allows responding medical personnel and other interested parties having a defibrillator support app installed on their mobile phone to seamlessly receive the Incident ID. Authorized medical personnel can use the Incident ID to retrieve the medical related incident information at any time. Other interested parties (e.g., family, friends, etc.) can provide the Incident ID to responders and/or treating physicians at any point in the post-incident treatment process.

During emergency use, the defibrillator broadcasts emergency status messages (and similar messages may be sent to any interface unit or other devices that are connected to the defibrillator by a physical connection) as represented by block 970. As previously mentioned, the emergency status message includes an Incident ID, which in the embodiment of FIG. 5(*b*) is the concatenation of the device identifier 422 and the activation timestamp 846. When desired, some or all of the broadcast emergency status messages may be configured as beacons. Listeners that receive the emergency status message 840 can handle appropriately as previously described. (Block 971). In some embodiments, the defibrillator support app executing on the listener stores the Incident ID in a locally created incident record (not shown) if it has not previously been stored. Block 975. The locally created incident record may store any information of interest that is available to the listener. The listener will continue to receive a series of emergency status messages as long as it remains within range of the defibrillator and the defibrillator remains in the emergency mode. However, the incident ID only needs to be stored once.

When the emergency incident terminates, the defibrillator will seek to transmit the incident file to the management server 300 if the file hasn't already been uploaded via another process. This can be accomplished a variety of ways. If the defibrillator is connected (wirelessly or via a wired connection) to an intermediate device (e.g., interface unit 200, a mobile communication device 105, etc.), it may send the incident file to the management server 300 via the connected intermediate device. Alternatively, if the defibrillator is not connected to an intermediate device at this stage, it will set the data available flag 445 to the "data available" state. Block 977. As such, subsequently sent status messages will make listeners aware that the defibrillator has information available that it would like to convey. Nearby listeners may prompt their users to request a connection or may attempt to automatically request/initiate such a connection as previously discussed. Block 979. When a suitable connection is made, the defibrillator will transfer the incident file to the connected listener which then passes the file on to the management server. Blocks 980, 981. The server then stores the incident file in an appropriate incident database. The stored incident file includes the Incident ID so that information in the file may be accessed by medical personnel as necessary and appropriate. As suggested above, such information may be useful to EMTs in route to a hospital, by doctors at the hospital, by physicians during follow-up care, etc.

The medical personnel may be informed of the Incident ID in a variety of ways. For example, if the EMT responder(s) have a suitable defibrillator support app installed on their Smartphone or other suitable mobile devices, they may seamlessly receive the Incident ID as listeners as outlined above. Alternatively, an interested bystander such as a family member, friend or volunteer responder with a suitable app may have access to the Incident ID and provide the ID to the medical personnel. One way of presenting the Incident ID to responders and/or bystanders is through the Incident Report shown in FIG. 14.

In some embodiments, the Incident ID can be linked to the victim's Medical ID (e.g. an Apple Medical ID) or other health related account on their phone. For example, a health app provided with or otherwise installed on a phone may be configured to handle defibrillator status messages and/or defibrillator generated beacons that include a medical ID. With that capability the victim's health app (as well as the health app of bystanders) will have the Incident ID. The app may include a tool or GUI mechanism that allows a user of the device to associate the Incident ID with their Medical ID. If desired, a notification or prompt can be generated at the listener after the emergency use is completed asking a user whether the current incident should be associated with the user's Medical ID. Associating the Incident ID with the victim's Medical ID on the victim's own Smartphone or other mobile devices, gives provides convenient mechanism for persistently storing the Incident ID in a manner that can be readily accessed when needed (e.g., in a hospital or during a follow-up visit) since many people are in the habit of carrying such devices with them most places that they go.

Although only a few embodiments of the invention have been described in detail, it should be appreciated that the invention may be implemented in many other forms without departing from the spirit or scope of the invention. For example, the nature of the status messages that are broadcast may vary widely, as may the specific information that is conveyed as part of any particular status message. The transmitted information may vary based on the operational state of the defibrillator (e.g. standby mode, emergency mode or other modes) and/or other factors including, but not limited to, the results of an internal status check, whether the defibrillator has been used, etc. The status messages may be configured as beacons or other advertising type packets.

As discussed above, the AED communications unit supports low energy broadcasts. In this context, the term broadcast refers to wirelessly transmitting information so that any device within range of the defibrillator that has the appropriate receiver and interpreter (listener) can receive and appropriately handle the broadcast information—without (a) requiring the establishment of a wireless connection between the transmitting AED and any receiving device; or (b) requiring the transmitting AED to be aware of the receiving device(s). This can be analogized to traditional AM or FM radio broadcasts where the transmitting device is generally unaware of what devices may be listening to its broadcasts. However, it should be appreciated that not requiring the transmitting AED to be aware of what devices are receiving its does not preclude the possibility that a broadcaster may be aware of a particular listener device's existence in some circumstances—as for example through a physical or wireless connection that is distinct from the broadcasts.

Some of the described embodiments contemplate the use of BLE 4.1 or 4.2 advertising packets which tend to have quite small payloads (e.g. 31 bytes of advertising data). It is expected that future BLE advertising protocols (e.g. BLE within Bluetooth 5, 5.1 etc.) and/or competing broadcast type advertising protocols may facilitate larger payloads which would provide the opportunity to expand the amount of information that is conveyed in any particular status message.

In some implementations, the AED may be configured to transmit multiple different advertisements at any given time, including beacons. The different advertisements may be directed at different users (e.g. the general public, the AED's authorized owner(s) and/or administrator(s), authenticated medical personnel or first responders, etc.). Alternatively or additionally, the multiple different advertisements may be configured to convey different types of information or simply convey more information than can be conveyed in a single message. In some embodiment different generally concurrent advertisements may be transmitted over different advertising channels, whereas in others, different advertisements may be transmitted sequentially over a single channel.

In some embodiments, a single advertisement may be transmitted over multiple advertising channels. This can be useful to increase the probability that any particular message will be successfully received by a listener when noise or competing communications interfering with a given channel.

The invention has been described primarily in the context of BLE advertisements which work very well for the intended purpose. However, it should be appreciated that there are a variety of other wireless protocols, including wireless protocols commonly used in home and office settings that can be configured to operate in a similar manner when desired and it is expected that new and improved protocols having advertising capabilities will continue to be developed. Thus, it should be appreciated that the inventions may be implemented using a variety of different wireless communications protocols.

The invention has also been described primarily in the context of the broadcast of status messages that provide information about the AED's current state. However, it should be appreciated that other types of information may be provided as well. For example, in some implementations it may be desirable to broadcast a URL (or mini-URL) that facilitates linking to a website that may contain pertinent information about the AED, the use of defibrillators in general, etc.

In some alternative embodiments, the BLE component (or other message broadcasting component) may be provided in a device that is physically attached to, but not a required part of the AED. For example, a wireless communication unit capable of performing the described functions may be provided in an optional interface unit or an optional supplemental battery pack that is attached to the AED, rather than being integrated into the AED.

The foregoing descriptions describe a number of functionalities performed by the listeners. Often such functions will be governed by a defibrillator support app containing programmed instructions stored in memory associated with the listener and designed to be executed on one or more processor associated with the listener. However, it should be appreciated that the functionality can be provided by a wide variety of different types of control algorithms and do not necessarily need to be performed by a defibrillator support app. The control algorithms can be implemented as programmed instructions (e.g. software or firmware) executing on a processor associated with the listener, via programmable or other logic, by hybrid combinations of the foregoing or in any other suitable manner.

As should be apparent from the foregoing description, the present embodiments should be considered illustrative and not restrictive and the invention is not to be limited to the details given herein, but may be modified within the scope and equivalents of the appended claims.

What is claimed is:

1. A method of handling a status message broadcast by a medical device using an advertisement type protocol, the status message including medical device status information, the method comprising:
   receiving the status message by a listening device, wherein the status message is received wirelessly by the listening device without establishing a connection between the medical device and the listening device;
   analyzing the received status message by the listening device and determining whether an action should be taken based at least in part on at least some of the medical device status information contained in the status message; and
   the listening device performing the action when it is determined that the action should be taken based at least in part on the medical device status information.

2. The method as recited in claim 1, wherein the determination that the action should be taken is based, at least in part, upon selected status information in the status message selected from the group consisting of:
   a current instruction state of the medical device;
   a current operating state of the medical device;
   an indication of a charge level of an internal battery in the medical device;
   an indication of a result of one or more self-test(s) performed by the medical device; and
   an indication of a firmware or software version currently installed on the medical device.

3. The method as recited in claim 1, wherein the action is or includes forwarding the received status message to a remotely located management server.

4. The method as recited in claim 3, further comprising:
   including a location identifier with the status message forwarded to the management server, the location identifier being created by the listening device and indicating a geographic location of the listening device at the time that the status message was received.

5. The method as recited in claim 3, further comprising including a timestamp that indicates a time that the status message was received by the listening device with the status message forwarded to the management server.

6. The method as recited in claim 5, further comprising, by the management server:
   determining whether the status message received from the listening device was transmitted by the medical device more recently than earlier received status messages from the medical device based at least in part on the timestamp; and
   when it is determined that the status message received from the listening device was transmitted by the medical device more recently than the earlier received status messages from the medical device, updating a database record associated with the medical device based on the status message received from the listening device.

7. The method as recited in claim 1 wherein the defibrillator status message is broadcast as one selected from the group consisting of: a wireless advertisement; a Bluetooth Low Energy (BLE) advertisement packet; a wireless beacon; an iBeacon; and an Eddystone Beacon.

8. The method as recited in claim 1, wherein the status message includes an information available indicator that indicates whether the medical device has new information available, the method further comprising:
   analyzing the received status message by the listening device and determining whether the information available indicator indicates that the medical device has new information available; and
   the listening device requesting or initiating a connection with the medical device when it is determined that the information available indicator indicates that the medical device has new information available.

9. The method as recited in claim 8, further comprising receiving the new information over the connection and at least one of:
   forwarding the new information to a management server;
   storing the new information at the listening device; and
   acting upon the new information by the listening device.

10. The method as recited in claim 1, wherein the status message includes a firmware or software version identifier that indicates a firmware or software version currently operational on the medical device, the method further comprising:
   analyzing the received status message by the listening device and determining whether the firmware or software version currently operational on the medical device is a most recent firmware or software version that is available for the medical device; and
   when the listening device determines that the firmware or software version currently operational on the medical device is not the most recent firmware or software version that is available for the medical device, the listening device directly or indirectly causes at least one of (i) a firmware or software update available prompt to be generated, or (ii) a firmware or software update to be delivered to the medical device.

11. The method as recited in claim 10, wherein the firmware or software update available prompt is rendered on the listening device.

12. The method as recited in claim 10, wherein the firmware or software update available prompt is delivered to an owner or administrator associated with the medical device.

13. The method as recited in claim 10, wherein the listening device determines the most recent firmware or software version for the medical device via a request sent to a remotely located server.

14. The method as recited in claim 10, wherein the firmware or software update is delivered to the medical device via the listening device.

15. A method comprising:
  by a listening device, receiving a beacon broadcast by a medical device, wherein the beacon includes defibrillator status information and is received wirelessly from the medical device without the establishment of a wireless connection between the medical device and the listening device; and
  generating a user notification on the listening device based at least in part on selected medical device status information contained in the beacon.

16. The method as recited in claim 15, wherein the user notification includes a GUI widget that facilitates accessing a report indicative of events that occurred, were detected, or were logged during use of the medical device.

17. The method as recited in claim 16, further comprising, in response to a user selection of the GUI widget, displaying at least portions of the report on a display screen associated with the listening device.

18. The method as recited in claim 16 wherein selection of the GUI widget causes activation of an app that directs a display of the report.

19. The method a recited in claim 15 further comprising:
  by the listening device, receiving a status message broadcast by the medical device using an advertisement type protocol, the status message being distinct from the beacon and received wirelessly by the listening device without establishing a connection between the medical device and the listening device; and
  displaying a report, wherein at least some information presented in the report is based, at least in part, on some of the status information contained in the status message.

20. The method as recited in claim 15 wherein the user notification is generated by a beacon handler executing in an operating system associated with the listening device without requiring any actions by an app responsible for directing the display of the incident report.

21. A method of handling a status message broadcast by a transmitting device using an advertisement type protocol, the method comprising:
  receiving the status message by a listening device, wherein the status message is received wirelessly by the listening device without establishing a connection between the transmitting device and the listening device; and
  forwarding the received status message from the listening device to a remotely located management server.

22. The method as recited in claim 21 wherein the listening device further sends supplemental information supplied by the listening device to the management server together with the status message.

23. The method as recited in claim 22 wherein the supplemental information includes a timestamp that indicates a time that the status message was received by the listening device.

24. The method as recited in claim 23 wherein the supplemental information includes a location of the listening device when the status message was received by the listening device.

25. A method as recited in claim 23 further comprising, by the management server:
  determining whether the status message received from the listening device was transmitted by the transmitting device more recently than earlier received status messages from the transmitting device based at least in part on the timestamp; and
  when it is determined that the status message received from the listening device was transmitted by the transmitting device more recently than the earlier received status messages from the transmitting device, updating a database record associated with the transmitting device based on information received from the listening device.

26. The method as recited in claim 22 wherein the supplemental information supplied by the listening device includes a location of at least one of the transmitting device and the listening device.

27. The method as recited in claim 26 wherein the location supplied by the listening device is a GNSS location of the listening device.

28. The method as recited in claim 27 further comprising, by the defibrillator management server, storing the GNSS location supplied by the listening device as a location of the transmitting device.

29. A method of handling a status message broadcast by a transmitting device, the method comprising:
  receiving the status message by a listening device, wherein the status message contains a firmware or software version identifier indicative of a current firmware or software version used by the transmitting device and wherein the status message is received by the listening device without establishing a connection between the transmitting device and the listening device;
  determining whether the current firmware or software version used by the transmitting device is a desired firmware or software version for use by the transmitting device based at least in part on the received firmware or software versions identifier; and
  when it is determined that the current firmware or software version used by the transmitting device is not the desired firmware or software version, facilitating delivery of a firmware or software update from a management server to the transmitting device via the listening device.

30. The method as recited in 29 wherein the firmware or software update is transmitted from the management server to the transmitting device via the listening device but is not persistently stored on the listening device.

31. The method as recited in claim 29 further comprising at least one of (i) initiating a first connection between the listening device and the transmitting device, and (ii) prompting a user to initiate the first connection between the listening device the transmitting device.

32. The method as recited in claim 31 further comprising initiating a second connection between the listening device and the management server to facilitate the delivery of the firmware or software update from the management server to the transmitting device via the listening device.

33. A non-transitory computer readable medium having programmed instructions configured to handle a status message wirelessly received by a listening device, wherein the status message was broadcast by a medical device and wirelessly received by the listening device without establishing a connection between the medical device and the listening device, wherein the programmed instructions are configured to:
  analyze the received status message and determine whether an action should be taken based at least in part on status information in the status message; and
  cause the action to be performed when it is determined that the action should be taken.

34. The non-transitory computer readable medium as recited in claim 33 wherein the programmed instructions are configured to cause the received status message to be forwarded to a remotely located management server.

35. The non-transitory computer readable medium as recited in claim 34 wherein the programmed instructions are further configured to cause a location identifier to be transmitted to the management server together with the forwarded status message, the location identifier indicating a geographic location of the listening device at the time that the defibrillator status message was received.

36. The non-transitory computer readable medium as recited in claim 33, wherein the programmed instructions are configured to:
  determine whether an information available indicator in the received status message indicates that the medical device has new information available; and
  request or initiate a connection with the medical device when it is determined that the information available indicator indicates that the medical device has new information available.

37. The non-transitory computer readable medium as recited in claim 36, wherein the programmed instructions are further configured to:
  facilitate the reception of the new information by the listening device from the defibrillator over the connection; and
  cause the new information to be forward from the listening device to a management server.

38. The non-transitory computer readable medium as recited in claim 33 wherein the programmed instructions are configured to:
  determine whether a firmware or software version currently operational on the medical device is a desired firmware or software version for the medical device based at least in part on a firmware or software version identifier contained in the status message; and
  when it is determined that the firmware or software version currently operational on the defibrillator is not the desired firmware or software version for the medical device, directly or indirectly cause at least one of, (a) a firmware or software update available prompt to be generated, and (b) a firmware or software update to be delivered to the medical device.

* * * * *

UNITED STATES PATENT AND TRADEMARK OFFICE
CERTIFICATE OF CORRECTION

| | |
|---|---|
| PATENT NO. | : 11,534,618 B2 |
| APPLICATION NO. | : 17/357498 |
| DATED | : December 27, 2022 |
| INVENTOR(S) | : Sturman et al. |

It is certified that error appears in the above-identified patent and that said Letters Patent is hereby corrected as shown below:

In the Specification

1. Column 6, Line 63, remove the "(" before "which".

2. Column 25, Line 31, remove the "(" before "e.g.".

In the Claims

1. In Line 1 of Claim 19 (Column 41, Line 38) change the "a" between "method" and "recited" to --as--.

2. In Line 1 of Claim 30 (Column 42, Line 56) insert --claim-- between "in" and "29".

3. In Line 5 of Claim 31 (Column 42, Line 64) insert --and-- between "device" and "the".

Signed and Sealed this
Eleventh Day of April, 2023

Katherine Kelly Vidal
*Director of the United States Patent and Trademark Office*